(12) United States Patent
Thomas et al.

(10) Patent No.: US 7,893,103 B2
(45) Date of Patent: Feb. 22, 2011

(54) PROCESSES FOR THE PREPARATION OF DPP IV INHIBITORS

(75) Inventors: Abraham Thomas, Navi Mumbai (IN); V. S. Prasada Rao Lingam, Navi Mumbai (IN); Ashok Bhausaheb Kadam, Navi Mumbai (IN); Suresh M. Kadam, Navi Mumbai (IN); Shantaram Kashinath Phatangare, Navi Mumbai (IN); Deepak Vitthal Ukride, Navi Mumbai (IN)

(73) Assignee: Glenmark Pharmaceuticals, S.A., La Chaux-de-Fonds (CH)

( * ) Notice: Subject to any disclaimer, the term of this patent is extended or adjusted under 35 U.S.C. 154(b) by 379 days.

(21) Appl. No.: 11/769,180

(22) Filed: Jun. 27, 2007

(65) Prior Publication Data

US 2008/0076818 A1    Mar. 27, 2008

Related U.S. Application Data

(60) Provisional application No. 60/807,327, filed on Jul. 13, 2006, provisional application No. 60/831,697, filed on Jul. 17, 2006.

(30) Foreign Application Priority Data

Jun. 27, 2006   (IN) ................ 1008/MUM/2006
Jun. 27, 2006   (IN) ................ 1009/MUM/2006

(51) Int. Cl.
*C07D 207/00*  (2006.01)
*A01N 43/36*   (2006.01)

(52) U.S. Cl. ...................... 514/423; 548/530
(58) Field of Classification Search ............ None
See application file for complete search history.

(56) References Cited

FOREIGN PATENT DOCUMENTS

| | | |
|---|---|---|
| EP | 1657237 | 5/2006 |
| WO | 03/002553 | 1/2003 |
| WO | 03/057666 | 7/2003 |
| WO | 2004/050654 | 6/2004 |
| WO | 2004/099185 | 11/2004 |
| WO | 2005/075426 A1 | 8/2005 |
| WO | 2006/011035 | 2/2006 |
| WO | 2006/040625 | 4/2006 |

OTHER PUBLICATIONS

Abraham, et al. Design, Synthesis, and Testing of Antisickling Agents. 2. 1a,b Proline Derivatives Designed for the Donor Site, J. Med. Chem. vol. 26, pp. 549-554, 1983.

Kawamoto, et al. A Convenient Synthesis of Versatile Side-chain Intermediates for Carbapenem Antibiotics, Synlett Letters, pp. 575-577, May 1995.

Kaspersen, et al. Unconventional Nucleotide Analogues. Part XIII.1 (2S,4S)-2-Hydroxy-methyl- and 2-Carboxy-4-(purin-9-yl) pyrrolidiness, J.C.S. Perkin I, pp. 1617-1622, 1975.

Oh, et al. Synthesis and antibacterial activity of 1?-methyl-2-(5-substituted thiazolo pyrrolidin-3-ylithio) carbapenem derivatives, European Journal of Medicinal Chemistry, vol. 37, pp. 743-754, 2002.

Thaning, et al. Anodic Methoxylation of Pyrrolidinol Derivatives.* Enantioselective Synthesis of cis- and trans-(3R)-3-Hydroxyprolines, Acta Chemica Scandinavica, vol. 43, pp. 290-295, 1989.

*Primary Examiner*—Yong Chu
*Assistant Examiner*—Sun Jae Y Loewe
(74) *Attorney, Agent, or Firm*—Blank Rome LLP

(57) ABSTRACT

The present invention relates to novel processes for preparing DPP-IV inhibitors having the structure of formula I,

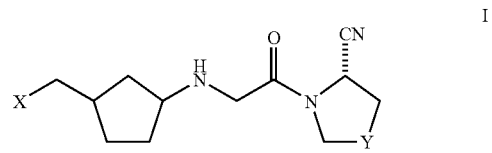

and pharmaceutically acceptable salt thereof, which are useful for treatment of Type 2 diabetes.

11 Claims, No Drawings

PROCESSES FOR THE PREPARATION OF DPP IV INHIBITORS

This application claims priority to Indian Patent Application No. 1008/MUM/2006, filed Jun. 27, 2006, Indian Patent Application No. 1009/MUM/2006, filed Jun. 27, 2006, U.S. provisional Application No. 60/807,327, filed Jul. 13, 2006, and U.S. Provisional Application No. 60/831,697, filed Jul. 17, 2006, all of which are incorporated by reference in their entireties.

FIELD OF THE INVENTION

The present invention relates to novel processes for preparing DPP-IV inhibitors having the structure of formula I,

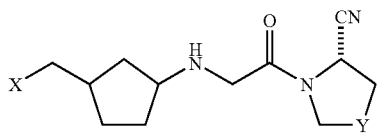

and pharmaceutically acceptable salt thereof, which are useful for treatment of Type 2 diabetes.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovasuclar and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus. DPP-IV inhibitors have been found to be useful for treating diabetes, and particularly Type II diabetes.

The present invention provides novel processes for preparing 1-[2-(cyclopentylamino)acetyl]pyrrolidine-2S-carbonitrile derivatives having the structure of formula I,

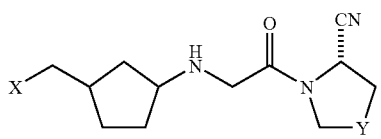

which are potent dipeptidyl peptidase IV (DPP-IV) inhibitors. The structural formula I bear two stereocentres on the cyclopentane ring and one or two stereocentres on the pyrrolidine ring.

Several structural variants of 1-[2-(cyclopentylamino) acetyl]pyrrolidine-2S-carbonitrile inhibitors of dipeptidyl peptidase IV (DPP-IV) have been described in PCT Publication Nos. WO 2005/075426, 2006/011035, 2006/040625, and U.S. Pat. Nos. 7,205,323, and 7,230,002

The U.S. Pat. No. 7,205,323 specifically describes and claims compounds of general formula I and related structural variants where 'X' is as defined hereinafter. The method disclosed for the preparation of compounds of the general formula I, involves coupling of a cyclopentylamine derivative of the general formula II with chloroacetyl-2S-cyanopyrrolidine derivative of the general formula III.

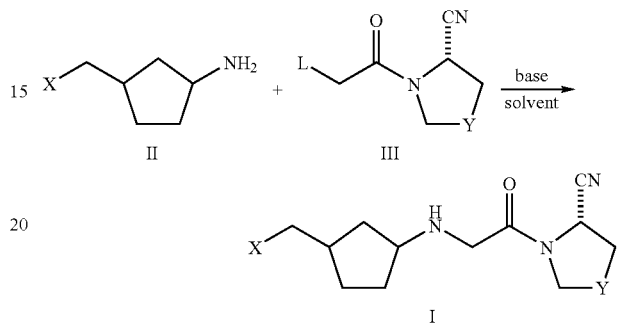

However, this coupling reaction suffered a number of drawbacks such as formation of significant levels of impurities, incomplete reaction, moderate yield and difficulty in isolation and purification of product due to the high aqueous solubility of the product. A major impurity which was formed under described coupling conditions was characterized as the dimeric product IV formed by dialkylation of intermediate II. This also necessitates the removal of unreacted intermediate II from the product. This impurity was formed up to 10-15% when a 1:1 mixture of intermediate II and intermediate III were used in the coupling reaction. The formation of dimeric impurity may be minimized by use of excess amine intermediate II in the coupling reaction, which affected the cost of the product. The relatively nonpolar dimeric impurity IV had a lower solubility, which further complicated the purification process.

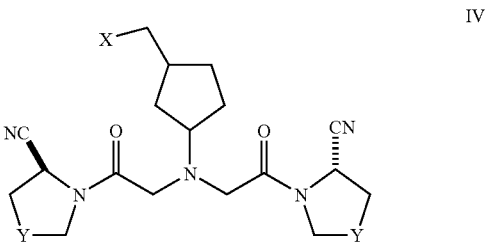

A large number of chemical transformations were required for the synthesis of intermediate II and III which affected the overall chemical yield of the product. The present invention describes a more efficient approach for the synthesis of compounds of the structural formula I in considerably fewer chemical steps and improved yields starting from commercially available (±)-2-azabicyclo[2.2.1]-hept-5-ene-3-one (Vince lactam) and a suitable proline derivative. Moreover, no chromatographic purification step is involved in the present process.

PCT Publication Nos. WO 2005/075421; 2004/099185; 2004/101514; 2003/074500 and 2004/009544; U.S. Publication No. 2004/0072892, and Japanese Publication No. JP 2004/244412, all of which are incorporated herein by reference in their entireties, disclose methods for preparing a compound of formula A described hereinafter. US 2004/0072892 and WO 2003/002553 disclose a process for the preparation of (2S,4S)-1-(bromoacetyl)-4-fluoropyrrolidine-2-carbonitrile. WO 2003/074500 discloses a process for the preparation of (2S,4S)-1-(chloroacetyl)-4-fluoropyrrolidine-2-carbonitrile. These processes for preparing compounds of formula A involve several steps, which significantly reduces the overall yield, thereby increasing their cost and time.

These processes also require tedious purification steps. In addition, the process in WO 2003/002553 utilizes diaminosulfur trifluoride (DAST) for fluorination, which is expensive and unstable at temperatures above 90° C. Furthermore, DAST is a flammable reagent with a flash point of 23° C.

Thus, the processes of the prior art present a number of practical difficulties that limit their use to relatively small scale applications. Therefore, there is a need for the development of a process which is amenable to scale-up and capable of practical application to large scale manufacturing. Understanding the importance of compounds of formula A as a key intermediate in the production of several DPP-IV inhibitors, there remains a need for alternative simple and cost-effective methods of preparing these compounds. The processes of the present invention for the preparation of a compound of formula A are convenient, efficient and easily scalable, and can function at high operative concentrations. Furthermore, the product of these processes can easily be worked up.

SUMMARY OF THE INVENTION

The present invention relates to novel processes for preparing DPPIV inhibitors, and pharmaceutically acceptable salt thereof, which are useful for treatment of Type 2 diabetes.

One embodiment of the present invention is a process for preparing a compound of formula I,

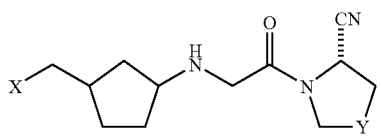

pharmaceutically acceptable salts, stereoisomers thereof, wherein X is a substituted or unsubstituted cycloalkyl, substituted or unsubstituted cycloalkenyl, substituted or unsubstituted aryl, substituted or unsubstituted aralkyl, substituted or unsubstituted heteroaryl, substituted or unsubstituted heterocyclic ring, substituted or unsubstituted heterocyclylalkyl, or substituted or unsubstituted heteroarylalkyl, and Y is $CH_2$ or CHF, which process comprises the following steps:

(a) condensing the compound of formula II with a glyoxalic acid ester

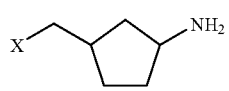

to give a compound of formula V,

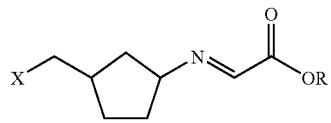

wherein R is $C_1$-$C_4$ alkyl, (b) reducing the imino group of the compound of the formula V to give an amine of formula VI,

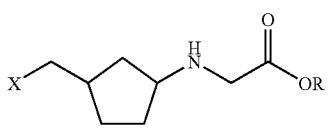

(c) N-protecting the compound of formula VI to give a glycine ester derivative of formula VII,

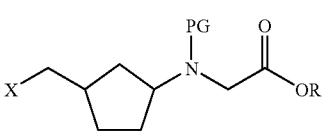

(d) hydrolyzing the compound of formula VII to give the glycine derivative of the formula VIII,

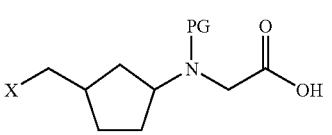

(e) coupling the compound of formula VIII with a prolinamide derivative to give a dipeptide derivative of formula IX,

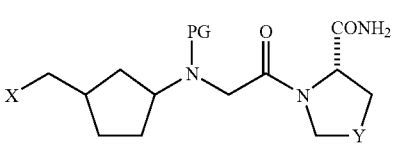

(f) converting the compound of formula IX to a nitrile derivative of formula X,

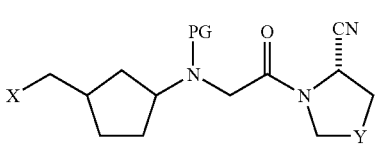

alternatively, coupling the compound of formula VIII with a 2S-cyanopyrrolidine derivative to give a compound of formula X, (h) deprotecting the compound of formula X to a compound of formula I

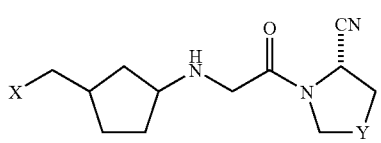

(i) converting the compound of formula I or X to a pharmaceutically acceptable salt of formula Ia,

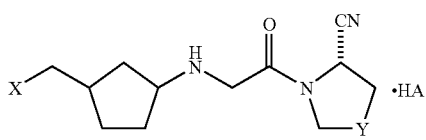

wherein HA is a suitable organic or inorganic acid, using the procedures known to a person of ordinary skill in the art.

Yet another embodiment is a process for preparing a compound of formula V,

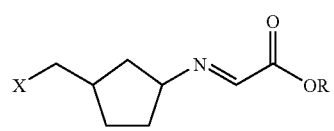

and stereoisomers thereof, wherein X is a substituted or unsubstituted cycloalkyl, substituted or unsubstituted cycloalkenyl, substituted or unsubstituted aryl, substituted or unsubstituted aralkyl, substituted or unsubstituted heteroaryl, substituted or unsubstituted heterocyclic ring, substituted or unsubstituted heterocyclylalkyl, or substituted or unsubstituted heteroarylalkyl, and R is $C_1$-$C_4$ alkyl, comprising the step of condensing the compound of formula II with a glyoxalic acid ester.

Preferably, the reaction is performed in one or more solvents, for example, chlorinated solvents (e.g., dichloromethane, dichloroethane or chloroform), hydrocarbon solvent (e.g., toluene, xylene or hexane) or a mixture thereof. The compound of formula V can be converted to a compound of formula I or a pharmaceutically acceptable salt thereof.

Another embodiment is a process for preparing a compound of formula VI,

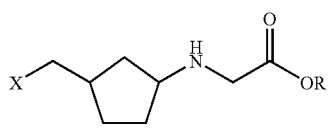

stereoisomers thereof, wherein X and R are as defined above, comprising the step of reducing imino group of the compound of formula V.

Suitable reducing agents include, but are not limited to, palladium, platinum, suitable borane reagent such as sodium cyanoborohydride. Preferably, the reduction is carried out in presence of palladium. The compound of formula VI can be converted to a compound of formula I or a pharmaceutically acceptable salt thereof.

Yet another embodiment is a process for preparing a compound of formula VII,

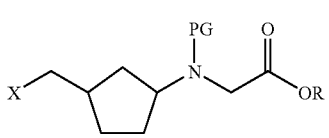

stereoisomers thereof, wherein X and R are as defined above, PG is a nitrogen protecting group, comprising the step of introducing nitrogen protecting group to the compound of formula VI.

Suitable nitrogen protecting groups include, but are not limited to, tert-butyloxycarbonyl, benzyloxy carbonyl, benzyl or optionally substituted benzyl. Preferably, the reaction is carried out in optional presence of a base such as alkali metal hydroxide (e.g., sodium hydroxide), organic base (e.g., triethylamine) or a mixture thereof, in one or more solvents, for example, ethers (e.g., tetrahydrofuran or dioxane), water, nitrites (e.g., acetonitrile or propionitrile). The compound of formula VII can be converted to a compound of formula I or a pharmaceutically acceptable salt thereof.

Yet another embodiment is a process for preparing a compound of formula VIII,

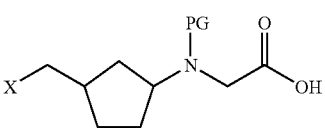

stereoisomers thereof, wherein X and PG are as defined above, comprising the step of hydrolyzing the compound of formula VII.

Suitable nitrogen protecting groups include, but are not limited to, tert-butyloxycarbonyl, benzyloxy carbonyl, benzyl or optionally substituted benzyl. Preferably, the reaction is carried out in presence of an inorganic base such sodium hydroxide, potassium hydroxide or barium hydroxide. The compound of formula VIII can be converted to a compound of formula I or a pharmaceutically acceptable salt thereof.

Yet another embodiment is a process for preparing a compound of formula IX,

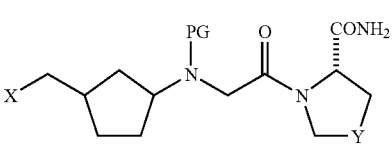

and stereoisomers thereof, wherein X and PG are as defined above, and Y is CH$_2$ or CF, comprising the step of coupling the compound of formula VIII with prolinamide derivative.

Suitable nitrogen protecting groups include, but are not limited to, tert-butyloxycarbonyl, benzyloxy carbonyl, benzyl or optionally substituted benzyl. Preferably, the reaction is carried out in presence of a coupling reagent such as dicyclohexylcarbodiimide (DCC), 1-(3-dimethylaminopropyl)-3-ethylcarbodiimide hydrochloride (EDC), BOP-chloride, ethyl chloroformate, or isobutyl chloroformate, in one or more solvents chlorinated solvents (e.g., dichloromethane or dichloroethane), water, nitriles (e.g., acetonitrile or propionitrile), polar aprotic solvents (e.g., dimethylformamide), acetates (e.g., ethyl acetate) or a mixture thereof. The compound of formula IX can be converted to a compound of formula I or a pharmaceutically acceptable salt thereof.

Yet another embodiment is a process for preparing a compound of formula X,

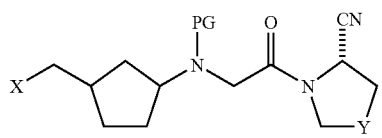

X and stereoisomers thereof, wherein X and PG are as defined above, and Y is CH$_2$ or CF, comprising the step of converting carboxamide of the compound of formula IX to nitrile; alternatively, the compound of formula X can also be prepared by coupling the compound of formula VIII with 2S-cyanopyrrolidine derivative.

Suitable nitrogen protecting groups include, but are not limited to, tert-butyloxycarbonyl, benzyloxy carbonyl, benzyl or optionally substituted benzyl. Preferably, the reaction is carried out in presence of strong dehydrating agents such as trifluoroacetic anhydride, phosphorous oxychloride (POCl$_3$), in an organic base such as triethylamine, disiopropylamine pyridine or imidazole. The compound of formula X can be converted to a compound of formula I or a pharmaceutically acceptable salt thereof.

Yet another embodiment is a process for preparing a compound of formula Ia,

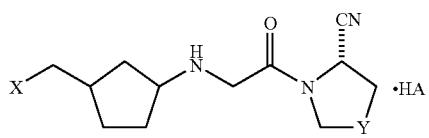

Ia and stereoisomers thereof, wherein X and Y are as defined above, comprising the step of converting the compound of formula X to formula Ia, wherein the conversion is characterized by one pot reaction.

Suitable HA includes, but are not limited to, hydrochloric acid, hydrobromic acid, sulfuric acid, phosphoric acid, maleic acid, fumaric acid, methanesulfonic acid, or benzoic acid. Preferably, the reaction is carried out in presence of a mineral acid or an organic acid, in a suitable solvent such as ethyl acetate.

Yet another embodiment is a pharmaceutical composition comprising:

(a) a compound of the formula

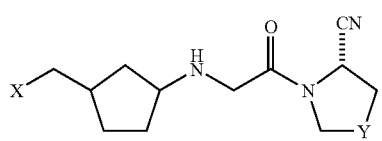

I or a pharmaceutically acceptable salt thereof, or a stereoisomer thereof, wherein X is a substituted or unsubstituted cycloalkyl, substituted or unsubstituted cycloalkenyl, substituted or unsubstituted aryl, substituted or unsubstituted aralkyl, substituted or unsubstituted heteroaryl, substituted or unsubstituted heterocyclic ring, substituted or unsubstituted heterocyclylalkyl, or substituted or unsubstituted heteroarylalkyl, and Y is CH$_2$ or CF, and (b) a compound selected from

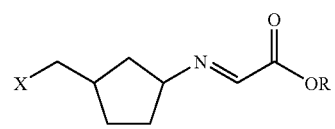

V

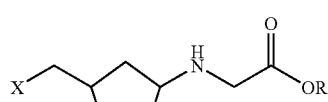

VI

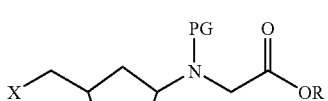

VII

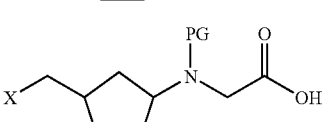

VIII

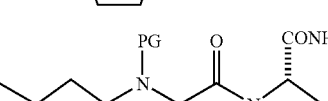

IX

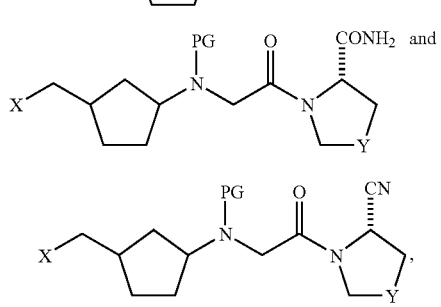

X wherein PG is a suitable nitrogen protecting group such as tert-butyloxycarbonyl, benzyloxy carbonyl, or benzyl, and X, R and Y are as defined above. Preferably, the compound in component (b) is present in an amount up to 0.2% (and more preferably up to 0.1%), based upon 100% total weight of components (a) and (b). The compound in component (a), i.e., the active component, is preferably present in an amount greater than 95% (and more preferably greater than 98% or 99%), based upon 100% total weight of components (a) and (b).

Yet another embodiment is a compound selected from compounds of the formulae

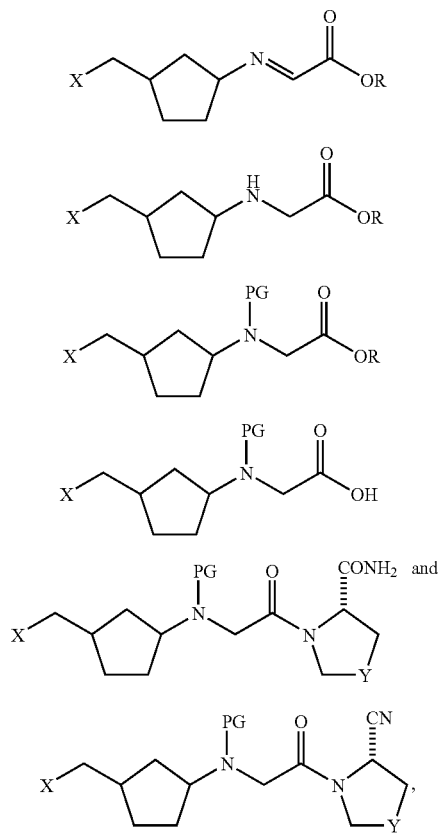

wherein X is a substituted or unsubstituted heteroaryl ring or a substituted or unsubstituted heterocyclic ring having at least one nitrogen atom, Y is $CH_2$ or CF, and PG is a suitable nitrogen protecting group such as tert-butyloxycarbonyl, benzyloxy carbonyl, or benzyl.

Processes described herein can include one or more of the following embodiments. For example, in one embodiment the compound of formula II can be converted into its enantiomerically pure or enantiomerically enriched isomers of formula IIa or IIb

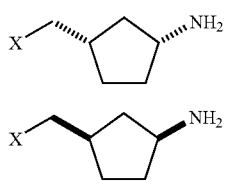

using the processes known to a person of ordinary skill in the art, including the process described hereinafter.

In another embodiment, the condensation reaction in step (a) is performed in one or more solvents, for example, chlorinated solvents (e.g., dichloromethane, dichloroethane or chloroform), hydrocarbon solvent (e.g., toluene, xylene or hexane) or a mixture thereof.

In another embodiment, the reduction in step (b) is carried out in presence of a suitable reducing agent such as palladium, platinum, borane reagents such as sodium cyanoborohydride. Preferably, the reduction is carried out in presence of palladium.

In another embodiment, the N-protection reaction in step (c) is carried out in optional presence of a base such as sodium hydroxide or triethylamine, in one or more solvents, for example, ethers (e.g., tetrahydrofuran or dioxane), water, nitriles (e.g., acetonitrile or propionitrile).

In another embodiment, the hydrolysis in step (d) is carried out in presence of an inorganic base such sodium hydroxide, potassium hydroxide or barium hydroxide.

In another embodiment, the coupling reaction in step (e) is carried out in presence of a coupling reagent such as dicyclohexylcarbodiimide (DCC), 1-(3-dimethylaminopropyl)-3-ethylcarbodiimide hydrochloride (EDC), BOP-chloride, ethyl chloroformate, or isobutyl chloroformate, in one or more solvents such as dichloromethane, dichloroethane, water, acetonitrile, dimethylformamide, ethyl acetate, or a mixture thereof.

In another embodiment, the reaction in step (f) is carried out in presence of a strong dehydrating agent such as trifluoroacetic anhydride, phosphoryl chloride, in an organic base such as triethylamine, diisopropylamine, pyridine or imidazole.

In another embodiment, the preferred compound of formula I is (2S,4S)-1-{2-[(3SR,1RS)-3-(1H-1,2,4-Triazol-1-ylmethyl)cyclopentylamino]acetyl}-4-fluoro-pyrrolidine-2-carbonitrile and its pharmaceutically acceptable salt.

According to another embodiment of the present invention, there are provided processes for preparing, 1-(chloroacetyl)-4-fluoropyrrolidine-2-carbonitrile, an intermediate, which can be used for the preparation of a compound of formula I,

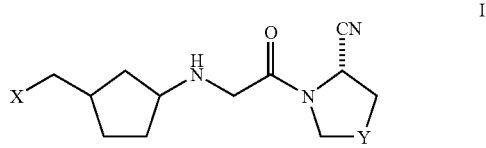

and a pharmaceutically acceptable salt thereof, wherein X and Y are the same as defined earlier.

Another embodiment of the present invention is a process for preparing a compound of formula A,

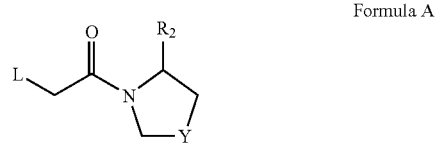

stereoisomers thereof, wherein L is a leaving group, Y is CHF, and $R^2$ is CN, which process comprises the steps of:

a) protecting an amide of formula XI

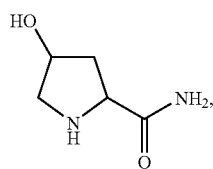

XI with a suitable nitrogen protecting group (PG) in ether solvent to form a compound of formula

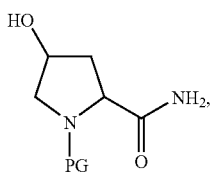

XII b) protecting the compound of formula XII with a suitable hydroxy protecting group ($Pg^1$) in presence of a base such as pyridine to form a compound of formula XIII

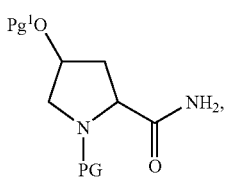

XIII c) dehydrating the compound of formula XIII in presence of a suitable dehydrating agent such as phosphorous oxychloride and a base such as pyridine to form a compound of formula XIV

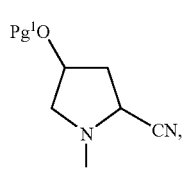

XIV d) deprotecting the compound of formula XIV with ammonia in alcoholic solvent such as methanol to form a compound of formula XV

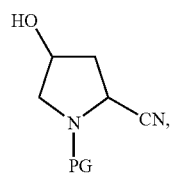

XV e) fluorinating the compound of formula XV with a suitable fluorinating agent such as diethylamino sulfurtrifluoride in chlorinated solvent such as dichloromethane to form a compound of formula XVI

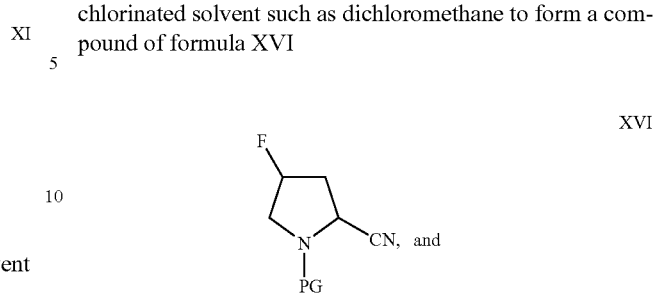

XVI f) deprotecting the compound of formula XVI and coupling it with an acetyl compound $L^2C(O)CH_2L$, [wherein $L^2$ is a leaving group (e.g., a halogen), (e.g., a haloacetyl halide, such as chloroacetyl chloride or bromoacetyl bromide)] in presence of p-toluenesulfonic acid and acetonitrile to form a compound of formula A.

This embodiment is described hereinafter in Method P.

In an alternative embodiment, the compound of formula XIII in the aforementioned process is formed by:

a) protecting an amide of formula XI

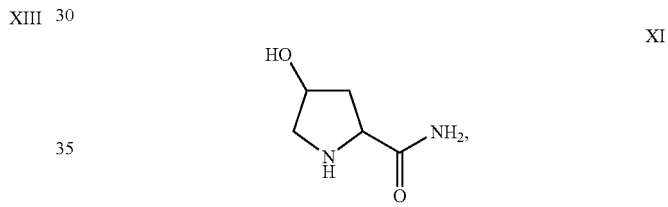

XI with a suitable hydroxy protecting group ($Pg^1$) to form a compound of formula XVII

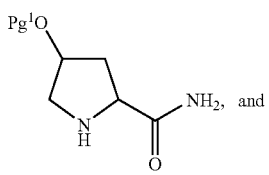

XVII b) protecting the compound of formula XVII with a suitable nitrogen protecting group (PG) to form a compound of formula XIII

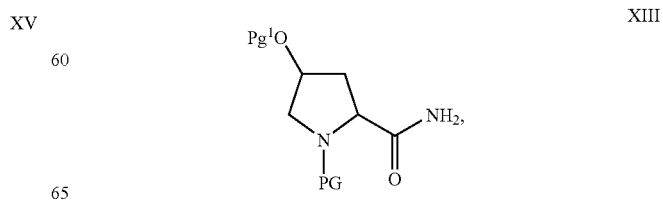

XIII

Method P can be used to prepare stereospecific compounds of formula A. For example, according to one preferred embodiment, compounds XI', XII', XVII', and XIII'-XVI' in Method P are as follows:

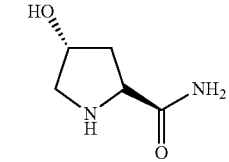

XI'

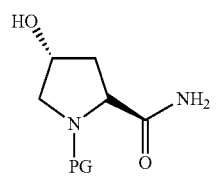

XII'

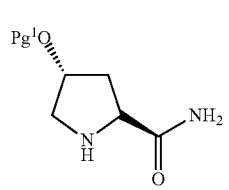

XVII'

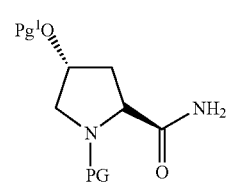

XIII'

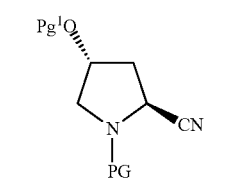

XIV'

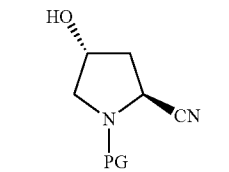

XV'

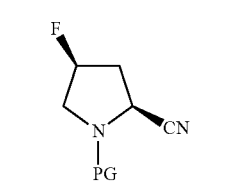

XVI'

Another embodiment is a method of preparing a compound of formula A, where L is a leaving group, Y is CHF, $R^2$ is CN, and PG and $Pg^1$ are as defined, by (1) performing at least one of steps (a), (b), (c), (d), or (e) of Method P, and (2) converting the product of step (1) in the compound of formula A. The conversion step can be performed by any method known in the art or described herein.

Yet another embodiment is a process for preparing a compound of formula A, wherein L, Y and $R^2$ are as defined above, comprising the steps of:

a) converting an ester of formula XVIII in presence of a base and a chlorinated solvent such as dichloromethane

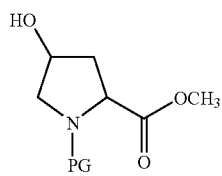

XVIII to a compound of formula XIX

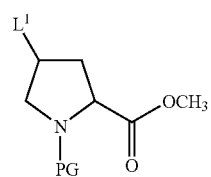

XIX wherein $L^1$ is a leaving group other than a halogen, b) aminating the compound of formula XIX with nitrogen-containing base such as ammonia in an alcoholic solvent such as methanol to form a compound of formula XX

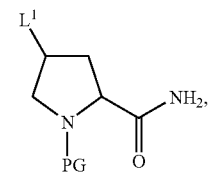

XX c) fluorinating the compound of formula XX with a fluorinating agent such as tetrabutylammonium fluoride in a solvent system such as tetrahydrofuran and water to form a compound of formula XXI

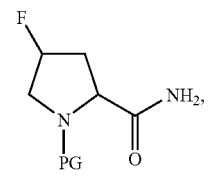

XXI d) dehydrating the compound of formula XXI with a suitable dehydrating agent such as phosphorous oxychloride in presence of base such as imidazole in pyridine to form a compound of formula XVI

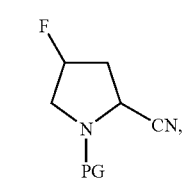

XVI e) deprotecting the compound of formula XVI and coupling it with an acetyl compound $L^2C(O)CH_2L$, [wherein $L^2$ is a leaving group (e.g., a halogen), (e.g., a haloacetyl halide, such as chloroacetyl chloride or bromoacetyl bromide)] in presence of p-toluenesulfonic acid and a base in acetonitrile to form a compound of formula A.

This embodiment is described hereinafter in Method Q.

Method Q can be used to prepare stereospecific compounds of formula A. For example, according to one preferred embodiment, compounds XVI' and XVIII'-XXI' in Method Q are as follows:

XVIII'
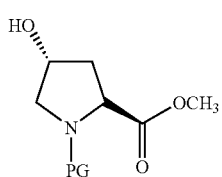

XIX'
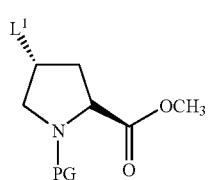

XX'
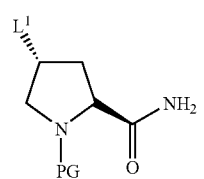

XXI'
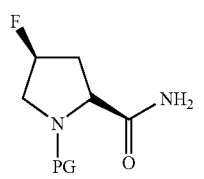

XVI'
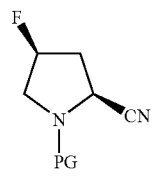

Yet another embodiment is a method of preparing a compound of formula A, where L is a leaving group, Y is CHF, $R^2$ is CN, and PG and $Pg^1$ are as defined, by (1) performing at least one of steps (a), (b), (c), or (d) of Method Q, and (2) converting the product of step (1) in the compound of formula A. The conversion step can be performed by any method known in the art or described herein.

Yet another embodiment is a pharmaceutical composition comprising:

(a) a compound of the formula

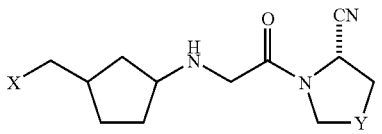

I or a pharmaceutically acceptable salt thereof, or a stereoisomer thereof, wherein X is a substituted or unsubstituted cycloalkyl, substituted or unsubstituted cycloalkenyl, substituted or unsubstituted aryl, substituted or unsubstituted aralkyl, substituted or unsubstituted heteroaryl, substituted or unsubstituted heterocyclic ring, substituted or unsubstituted heterocyclylalkyl, or substituted or unsubstituted heteroarylalkyl, and Y is $CH_2$ or CF, and (b) a compound selected from XI
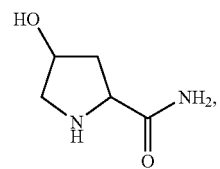

XII
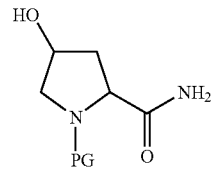

XIII
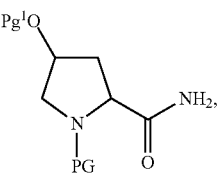

XIV
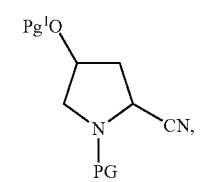

XV
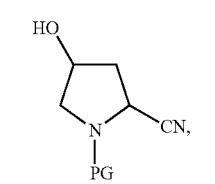

XVI
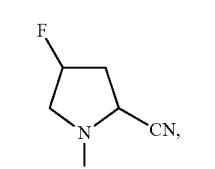

-continued

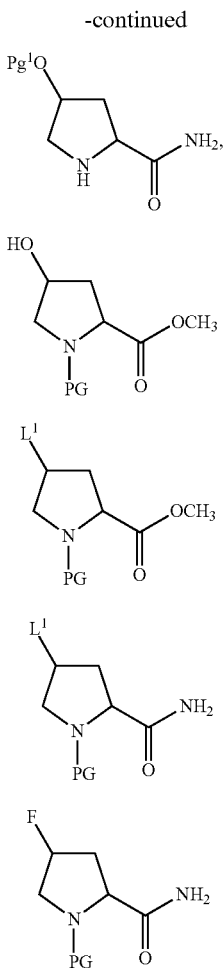

wherein PG, Pg¹ and L¹ are as defined above. Preferably, the compound in component (b) is present in an amount up to 0.2% (and more preferably up to 0.1%), based upon 100% total weight of components (a) and (b). The compound in component (a), i.e., the active component, is preferably present in an amount greater than 95% (and more preferably greater than 98% or 99%), based upon 100% total weight of components (a) and (b).

Yet another embodiment is a compound selected from compounds of the formulae

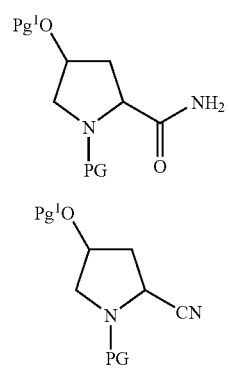

-continued

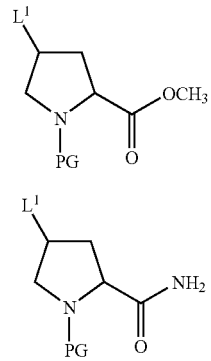

wherein PG, Pg¹ and L¹ are the same as defined earlier.

The compound of formula A can be converted to a compound of formula I

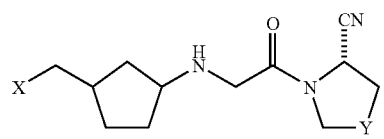

pharmaceutically acceptable salts, stereoisomers thereof, wherein X is a substituted or unsubstituted cycloalkyl, substituted or unsubstituted cycloalkenyl, substituted or unsubstituted aryl, substituted or unsubstituted aralkyl, substituted or unsubstituted heteroaryl, substituted or unsubstituted heterocyclic ring, substituted or unsubstituted heterocyclylalkyl, or substituted or unsubstituted heteroarylalkyl, and Y is $CH_2$ or CHF, using the procedure described in WO 2006/040625.

DETAILED DESCRIPTION OF THE INVENTION

Definition of Terms as Used Herein

The compounds of the present process invention may contain up to four asymmetric carbon centres and thus occur as racemic mixtures, single enantiomers, diastereomeric mixtures and individual diastereomers. Each asymmetric carbon centre independently produces two optical isomers and it is intended that all of the possible optical isomers and diastereomers and mixtures are included in the process invention. The term "enantiomeric excess" is synonymous with the term "optical purity."

The term "alkyl" refers to both straight and branched configuration containing no unsaturation. Examples of such alkyl groups are methyl, ethyl, propyl, isopropyl, butyl tertiary butyl and the like. The term "heteroaryl ring" refers to 5- or 6-membered aromatic heterocycle that contains at least one heteroatom selected from O, S and N. Heteroaryls also include heteroaryls fused to other rings such as aryls and cycloalkyls. Examples of heteroaryls include, but are not limited to pyrrole, indole, imidazole, 1,2,3-triazole, 1,2,4-triazole, tetrazole, and the like as defined in the U.S. Pat. No. 7,205,323. The term "heterocycle" refers to 4 and 7 membered ring radical containing atoms selected from O, S and N. Examples of heterocycles include, but not limited to pyrrolidine, piperidine, thiazolidine, 2,3-dihydroindolyl, dihydroisoindolyl and the like as defined in the U.S. Pat. No. 7,205,323.

The term "cycloalkyl" denotes a non-aromatic mono or multicyclic ring system of about 3 to 12 carbon atoms such as cyclopropyl, cyclobutyl, cyclopentyl, cyclohexyl and examples of multicyclic cycloalkyl groups include perhydronapththyl, adamantyl and norbornyl groups bridged cyclic group or spirobicyclic groups e.g. spiro(4,4) non-2-yl.

The term "cycloalkylalkyl" refers to cyclic ring-containing radicals containing in the range of about 3 up to 8 carbon atoms directly attached to alkyl group which are then attached to the main structure at any carbon from alkyl group that results in the creation of a stable structure such as cyclopropylmethyl, cyclobutylethyl, cyclopentylethyl, and the like.

The term "cycloalkenyl" refers to cyclic ring-containing radicals containing in the range of about 3 up to 8 carbon atoms with at least one carbon-carbon double bond such as cyclopropenyl, cyclobutenyl, cyclopentenyl and the like.

The term "aryl" refers to aromatic radicals having in the range of 6 up to 14 carbon atoms such as phenyl, naphthyl, tetrahydronapthyl, indanyl, biphenyl and the like.

The term "arylalkyl" refers to an aryl group as defined above directly bonded to an alkyl group as defined above. e.g., —$CH_2C_6H_5$, —$C_2H_5C_6H_5$ and the like.

The term "heterocyclic ring" refers to a stable 3- to 15 membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl chromanyl, isochromanyl and the like.

The term "heteroaryl" refers to heterocyclic ring radical as defined above. The heteroaryl ring radical may be attached to the main structure at any heteroatom or carbon atom that results in the creation of a stable structure.

The heterocyclic ring radical may be attached to the main structure at any heteroatom or carbon atom that results in the creation of a stable structure.

The term "heteroarylalkyl" refers to heteroaryl ring radical as defined above directly bonded to alkyl group. The heteroarylalkyl radical may be attached to the main structure at any carbon atom from alkyl group that results in the creation of a stable structure.

The term "heterocyclyl" refers to a heterocyclic ring radical as defined above. The heterocyclyl ring radical may be attached to the main structure at any heteroatom or carbon atom that results in the creation of a stable structure.

The term "heterocyclylalkyl" refers to a heterocyclic ring radical as defined above directly bonded to alkyl group. The heterocyclylalkyl radical may be attached to the main structure at carbon atom in the alkyl group that results in the creation of a stable structure.

The substituents in the 'substituted arylalkyl' 'substituted aryl' 'substituted heterocyclic ring', 'substituted heteroaryl ring,' 'substituted heteroarylalkyl', 'substituted heterocyclylalkyl ring', may be the same or different and are selected from hydrogen, hydroxy, halogen, carboxyl, cyano, nitro, oxo (=O), thio(=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, 'substituted heterocyclylalkyl ring' substituted or unsubstituted heteroarylalkyl, substituted or unsubstituted heterocyclic ring, substituted or unsubstituted guanidine, —$COOR^x$, —$C(O)R^x$, —$C(S)R^x$, —$C(O)NR^xR^y$, —$C(O)ONR^xR^y$, —$NR^xCONR^yR^z$, —$N(R^x)SOR^y$, —$N(R^x)SO_2R^y$, —$(=N—N(R^x)R^y)$, —$NR^xC(O)OR^y$, —$NR^xR^y$, —$NR^xC(O)R^y$—, —$NR^xC(S)R^y$—$NR^xC(S)NR^yR^z$, —$SONR^xR^y$—, —$SO_2NR^xR^y$—, —$OR^x$, —$OR^xC(O)NR^yR^z$, —$OR^xC(O)OR^y$—, —$OC(O)R^x$, —$OC(O)NR^xR^y$, —$R^xNR^yC(O)R^z$, —$R^xOR^y$, —$R^xC(O)OR^y$, —$R^xC(O)NR^yR^z$, —$R^xC(O)R^x$, —$R^xOC(O)R^y$, —$SR^x$, —$SOR^x$, —$SO_2R^x$, —$ONO_2$, wherein $R^x$, $R^y$ and $R^z$ is selected independently for each occurrence from the group of hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, 'substituted heterocyclylalkyl ring' substituted or unsubstituted heteroarylalkyl, substituted or unsubstituted heterocyclic ring.

The term "inorganic acid" or "mineral acid" refers to, but is not limited to, HCl, HBr, $H_2SO_4$, phosphoric acid and the like. The term "organic acid" refers to, but is not limited to, formic acid, acetic acid, trifluoroacetic acid, propionic acid, methanesulfonic acid, p-toluene sulfonic acid and the like.

The term "base" includes both, organic and inorganic bases. Organic bases include, but are not limited to, triethylamine, diisopropylamine, diisopropylethylamine, pyridine, imidazole, and bicyclic amines, such as DBN and DBU. The term organic base also includes anionic nitrogen bases, such as lithium diisopropylamide, potassium bis(trimethylsilylamide) and the like. The term "inorganic base" includes, but is not limited to, NaH, NaOH, KOH, LiOH and alkali metal carbonates such as potassium carbonate, sodium carbonate, lithium carbonate, sodium bicarbonate, cesium carbonate and the like.

The term "coupling reagents" include dicyclohexylcarbodiimide (DCC), 1-(3-dimethylaminopropyl)-3-ethylcarbodiimide hydrochloride (EDC), Benzotriazol-1-yloxytris(dimethylamino)phosphoniumhexafluorophosphate (BOP), O-(1H-Benzotriazol-1-yl)-N,N,N',N'-tetramethyluronium hexafluorophosphate (TBTU), ethyl chloroformate, isobutyl chloroformate and the like. Suitable solvents for the amide coupling include water, $CH_3CN$, DMF, DMA, dichloromethane, ethyl acetate and the like and mixtures thereof.

Pharmaceutically acceptable salts forming part of this invention include salts derived from HCl, HBr, $H_2SO_4$, phosphoric acid, maleic acid, fumaric acid, methanesulfonic acid, p-toluenesulfonic acid, benzoic acid, salicylic acid, nicotinic acid and the like. For a description of pharmaceutically acceptable salts see: Stahl, P. H. and Wermuth, C. G. (Eds.). "Handbook of Pharmaceutical Salts, Properties, Selection, and Use" Wiley-VCH, New York, 2002.

The term "leaving group" includes substituents that can be displaced in a nucleophilic substitution or elimination. Suitable leaving groups include, but are not limited to, halogens (such as bromine and chlorine), methanesulfonyloxy ("OMs") and p-toluenesulfonyloxy ("OTs"). Other suitable leaving groups will be apparent to those of skill in the art.

The term "protecting group" refers to a substituent that is employed to block or protect a particular functionality. Other functional groups on the compound may remain reactive. For example, a "nitrogen protecting group" is a substituent attached to a nitrogen atom that blocks or protects the functionality of the nitrogen atom in the compound. Suitable nitrogen protecting groups (PG) include, but are not limited to, acetyl, trifluoroacetyl, t-butyloxycarbonyl (BOC), benzyloxycarbonyl (CBz) and 9-fluorenylmethylenoxycarbonyl (Fmoc), benzyl, substituted benzyl. Similarly, a "hydroxy protecting group" refers to a substituent to a hydroxy group that blocks or protects the hydroxy functionality. Suitable hydroxy protecting groups ($Pg^1$) include, but are not limited to, benzyl, benzoyl, acetyl and silyl. For a general description of protecting groups and their use, see T. W. Greene, Protective Groups in Organic Synthesis, John Wiley & Sons, New York, 1991, which is hereby incorporated by reference.

Suitable dehydrating agents include, but are not limited to, phosphorus oxychloride, phosphorus pentaoxide, sulfuric acid, phosphonitrilic chloride and the like.

Suitable fluorinating agents include, but are not limited to, diethylamino sulfurtrifluoride, selectfluor, tetrabutylammonium fluoride (TBAF), N-fluoropyridinium triflate and the like. A preferred fluorinating agent is TBAF.

Salts can be obtained by dissolving the free compound in a suitable solvent, e.g., in a chlorinated hydrocarbon, such as methylene chloride or chloroform, or a low molecular weight aliphatic alcohol (e.g., ethanol and isopropanol) which contains the desired acid or base, or to which the desired acid or base is then added. The salts are obtained by filtering, re-precipitating, precipitating with a non-solvent for the addition salt or by evaporating the solvent. Salts obtained can be converted by basification or by acidifying into the free compounds which, in turn, can be converted into salts.

Representative synthetic schemes which are part of the present invention are detailed below. The synthetic schemes are for the purpose of illustration of the new process and are not intended to limit the scope of the present process and the diverse use of the hitherto unreported intermediates. It is understood that anyone who is skilled in the art of organic synthesis would be able to generalize these synthetic transformations for the synthesis of diverse library of compounds.

Synthetic Methods

A process for the synthesis of intermediate of the formula II where X is 1,2,4-triazole is given in Scheme 1. Thus, commercially available (±)-2-azabicyclo[2.2.1]hept-5-ene-3-one 1 (available from Lonza, Switzerland; Suzhou Kaiyuan Minsheng Chemicals Technology Co. Ltd. Qunxing, China) is treated with di-tert-butyl dicarbonate in the presence of triethylamine and catalytic amounts of dimethylaminopyridine in a solvent such as tetrahydrofuran to give intermediate 2 in quantitative yield. Catalytic hydrogenation of 2 followed by reductive cleavage of the saturated bicyclic amide 3 gives hydroxylmethyl cyclopentylamine derivative 4 in excellent yield. The triazolylmethyl derivative 7 can be prepared using two approaches as shown in the Scheme. The hydroxyl group was converted to the corresponding methanesulfonate and treated with 1,2,4-triazole in tetrahydrofuran in the presence of a strong base such as sodium hydride to give 7. Alternatively, the alcohol 4 can be converted to 7 in one step by using a Mitsunobu reaction using triphenylphosphine and diethyl azodicarboxylate in tetrahydrofuran at elevated temperature. The BOC protecting group was removed under acidic conditions to give the cis-racemic amine 7 in good yield.

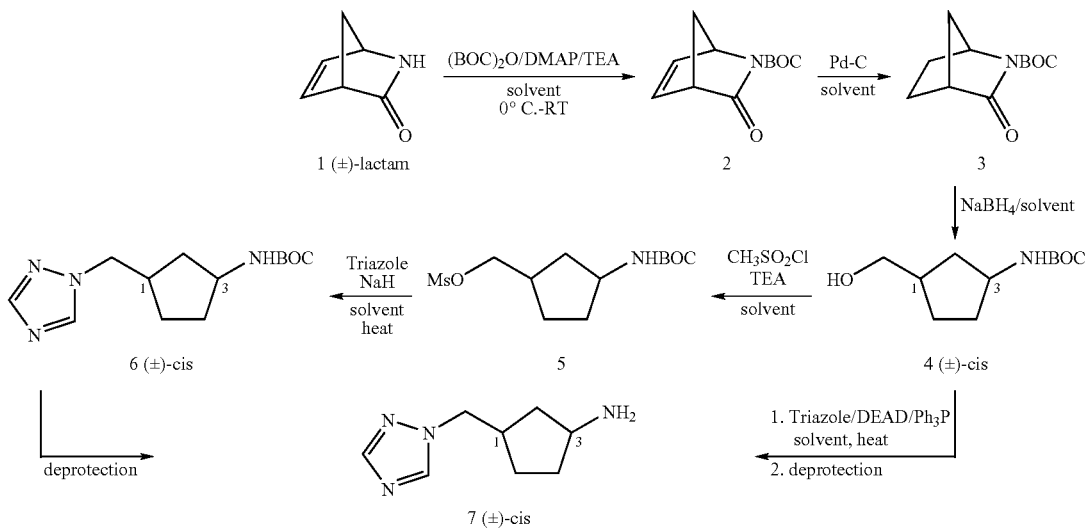

Scheme 1

A process for the optical resolution of intermediate of the formula II where X is 1,2,4-triazole is given in Scheme 2. Representative examples of chiral resolving agents used for the resolution of racemic intermediate 7 along with enantiomeric ratio are given in Table 1. The diastereomeric salt precipitated out was collected and treated with a base to release the enriched amine. The amines thus obtained were analyzed by chiral HPLC to determine the enantiomeric ratio. In some selected cases (entries 3, 4 and 10) diastereomeric salts were recrystallised to further improve the optical purity of the enriched isomer.

TABLE 1

Details of resolution of cis-(±)-1-(1,2,4-Triazol-1-ylmethyl)-3-cyclopentylamine using chiral carboxylic acids

| No. | Resolving agent | Solvent | Ratio of Enantiomers (8:9) | |
| --- | --- | --- | --- | --- |
| | | | Before Crystallization | After crystallization |
| 1 | Dibenzoyl-L-tartaric acid | Ethanol | 60.6:39.4 | — |
| 2 | Dibenzoyl-L-tartaric acid | Acetone-methanol (80:20) | 62.8:37.2 | — |
| 3 | Dibenzoyl-L-tartaric acid | Methanol-toluene (50:50) | 89.2:10.8 | 97.1:2.9 |
| 4 | Dibenzoyl-L-tartaric acid | Methanol-acetonitrile (35:65) | 92.4:7.6 | 99.8:0.2 |
| 5 | Di-p-toluyl-L-tartaric acid | Methanol-acetonitrile (20:80) | 60.8:39.2 | — |
| 6 | Di-p-toluyl-L-tartaric acid | Methanol-isopropanol | 81.4:18.6 | — |
| 7 | (R)-(−)-Camphor sulfonic acid | Acetonitrile | 52.7:47.3 | — |
| 8 | (S)-(+)-Mandelic acid | Isopropanol | 56.6:43.4 | — |
| 9 | N-Tosyl-L-proline | Ethanol | 27.1:72.9 | — |
| 10 | Dibenzoyl-D-tartaric acid | Methanol-acetonitrile (35:65) | 9.2:90.8 | 0.6:99.4 |

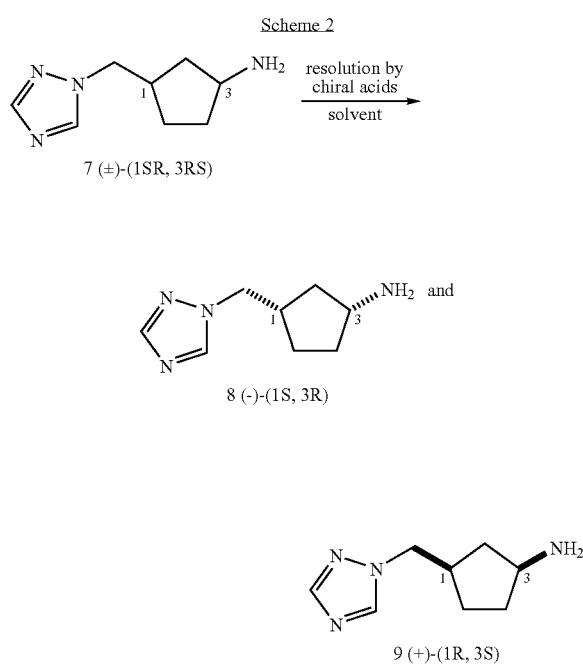

A process for the synthesis of compounds of the structural formula VII, where X is 1,2,4-triazole is given in Scheme 3. Thus, as a representative example to demonstrate this process invention, one of the pure enantiomers, (1R,3S)-3-1,2,4-triazol-1-ylmethyl)cyclopentan-1-amine 8 was condensed with commercially available ethyl glyoxylate in dichloromethane in the presence of anhydrous sodium sulfate to give the imine ester 10 in quantitative yield. The imine ester 10 was on Pd catalyzed hydrogenation afforded glycine ester 11 in quantitative yield. The amino group was protected as BOC derivative and the ester group is hydrolyzed under basic conditions to give glycine derivative 12 in excellent yield.

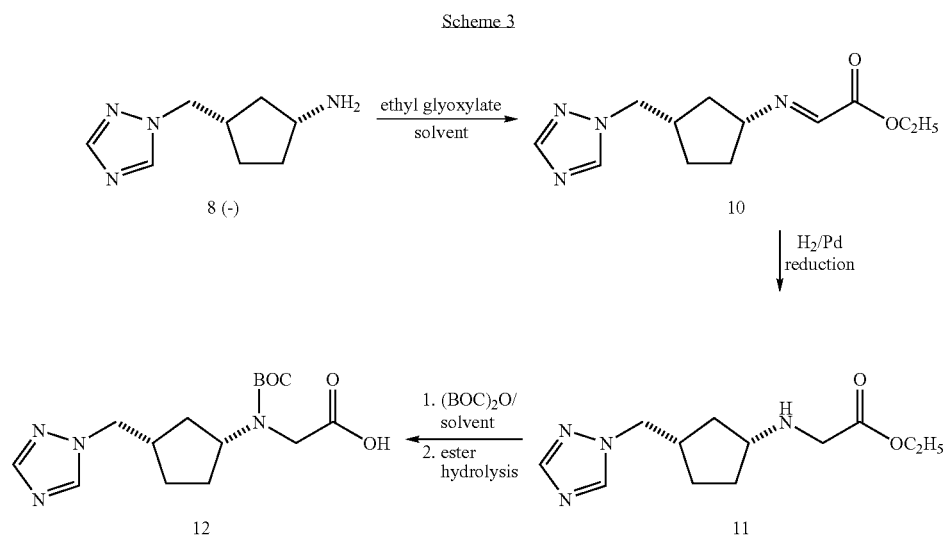

A process for the synthesis of stable non-racemic salts of proline derivatives from commercially available N—BOC-(2S,4S)-4-fluoroproline (available from Sumitomo Corporation, Tokyo, Japan; Tosoh F-Tech Inc., Japan) is given in Scheme 4. Thus, amino group protected 2S,4S-4-fluoroproline 13 is converted to a mixed anhydride by reaction of 13 with ethyl chloroformate in the presence of a suitable base such as triethylamine followed by treatment with aqueous ammonia to give the corresponding prolinamide derivative 14 in nearly quantitative yield. Intermediate 14 is deprotected under acidic conditions to give the prolinamide salt 15, which is suitable for direct coupling with acid 12. Alternatively, the carboxamide group in 14 is transformed to the corresponding nitrile group using a dehydrating agent (e.g. trifluoroacetic anhydride) under basic reaction conditions to give the nitrile 16. A stable salt of 2S-cyanoproline derivative 17 is obtained by treating 16 with a suitable mineral acid or organic acid in a suitable organic solvent.

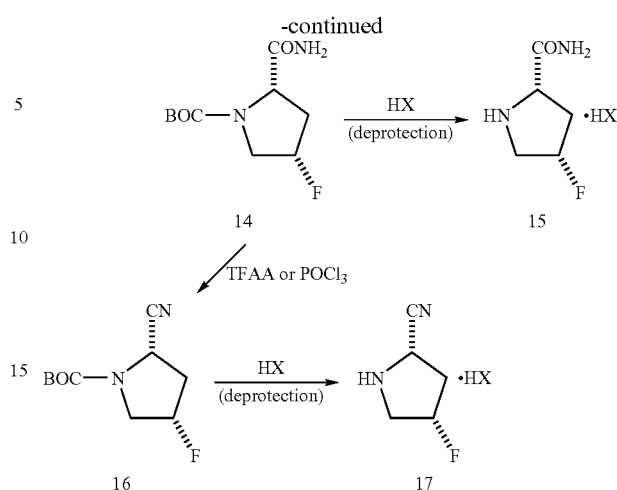

Scheme 4

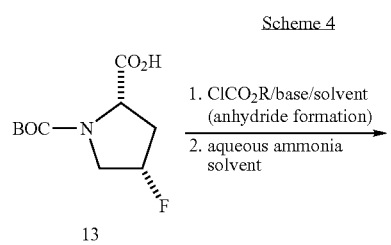

A process for coupling a glycine intermediate of the general formula VIII with a proline derivative is shown in Scheme 5. Two approaches are shown in the scheme to demonstrate the broad scope and utility of the present process invention for the preparation of DPP-IV inhibitors of the general formula I. In one approach, intermediate 12 is coupled with (2S,4S)-4-fluoroprolinamide salt in the presence of a suitable coupling agent to give dipeptide derivative 20 in good yield. The carboxamide group of 20 is converted to the corresponding nitrile and the BOC group is cleaved under acidic conditions to give 19 in good yield. In the second approach, 12 is coupled with 17 to give the cyanoproline amide derivative 18, which on deprotection gives 19 in excellent yields.

Scheme 5

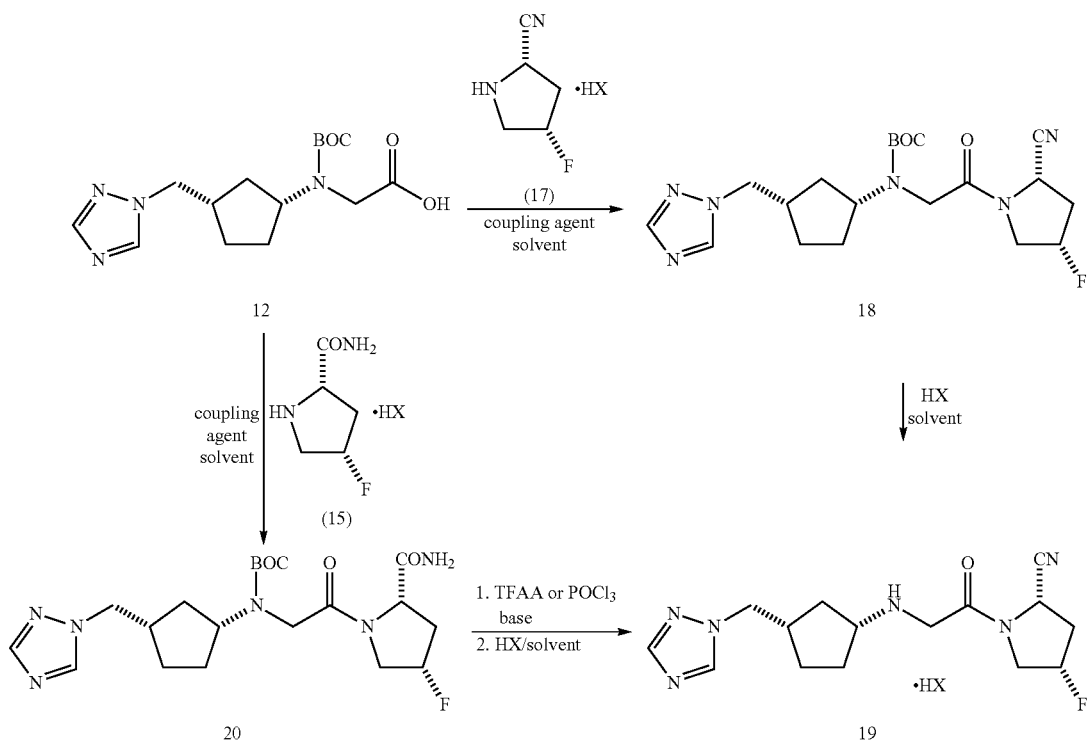

Scheme 6 (Method P)

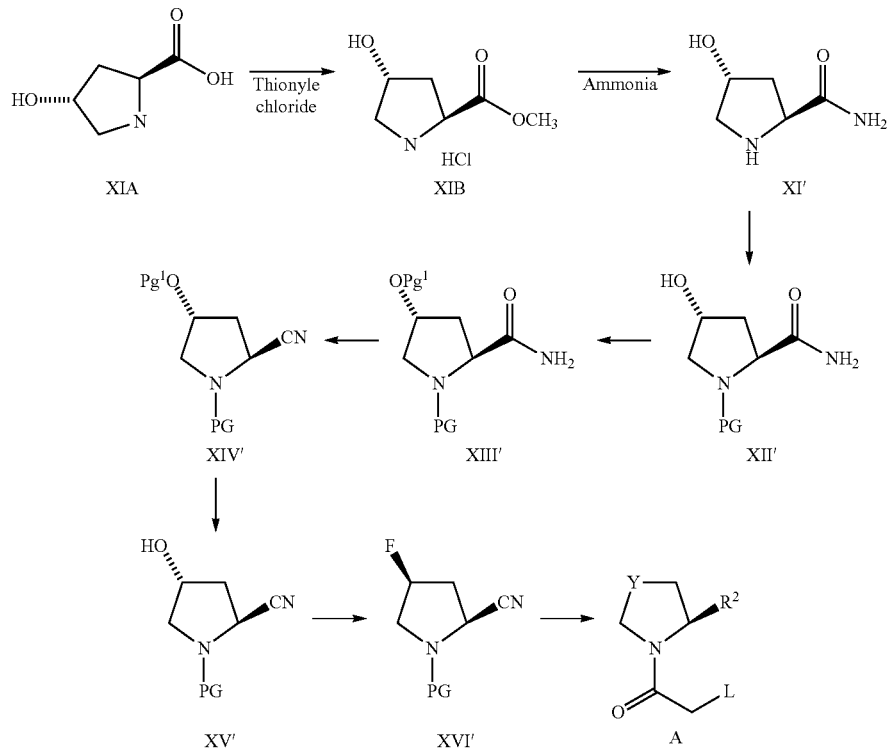

Method P involves protecting the nitrogen atom in the pyrrolidine ring of a compound of formula XI', such as by reacting it with BOC-anhydride, for example, in an ether solvent at about 30° C., to provide a compound of formula XII'. Compound XI XI' is commercially available and can be synthesized by the method described in GB 1246141, which is hereby incorporated by reference. The hydroxyl group of compound XII' is protected, such as by reacting it with benzoyl chloride, for example in pyridine at about 30° C., to form a compound of formula XIII'. Compound XIII' is dehydrated, such as by reacting it with phosphorous oxychloride, for example in pyridine at about 30° C., to form a compound of formula XIV XIV'. The hydroxyl group of compound XIV' is deprotected, such as by reacting it with ammonia, for example, in methanol at about 10° C., to form a compound of formula XV'. Compound XV' is fluorinated, such as by reacting it with diethylamino sulfurtrifluoride, for example in dichloromethane at about 30° C., to form a compound of formula XVI'. Compound XVI' is deprotected and coupled to an acetyl compound, such as by reacting it with chloroacetyl chloride, for example in the presence of p-toluenesulfonic acid and a base (preferably in acetonitrile), to form a compound of formula A.

Scheme 6 (Method Q)

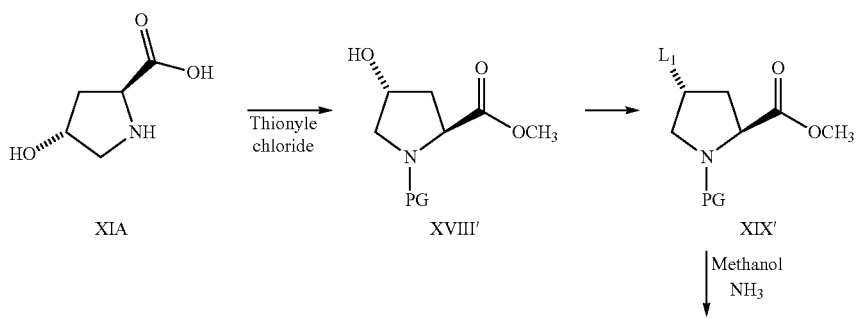

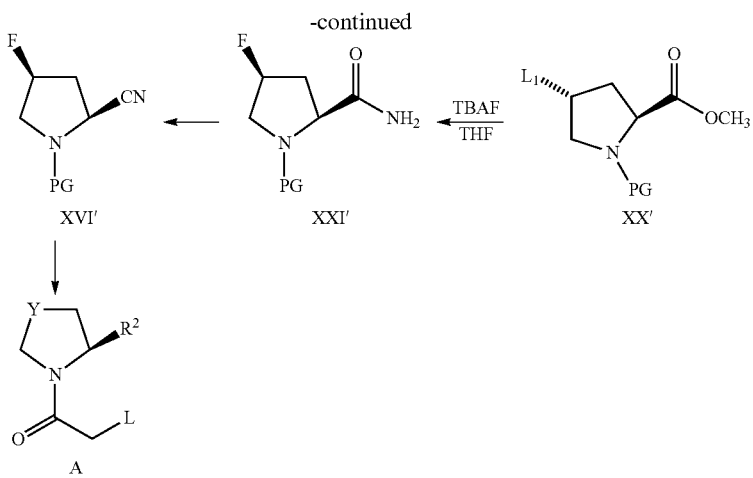

Method Q involves converting the compound of formula XVIII' to a compound of formula XIX', such as by reacting it with methylsulfonyl chloride, for example, in dichloromethane and an inorganic base at about 0-5° C. Compound XIX' is aminated, such as by reacting it with ammonia, for example under pressure in methanol at about 25-35° C., to form a compound of formula XX'. Compound XX' is then fluorinated, such as by reacting it with tetrabutylammonium fluoride (TABF), for example, in a biphasic mixture of tetrahydrofuran (THF) and water at about 25-35° C., to form a compound of formula XXI'. Compound XXI' is dehydrate, such as by reacting it with phosphorus oxychloride, for example in the presence of imidazole in pyridine at about 0-5° C., to form a compound of formula XVI'. Compound XVI' is deprotected and coupled to an acetyl compound $L^2C(O)CH_2L$, such as by reacting it with chloroacetyl chloride, for example in the presence of p-toluenesulfonic acid and a base (e.g., acetonitrile), to form a compound of formula A.

According to one preferred embodiment, TABF is employed as the fluorinating agent. TABF is soluble in polar organic solvents and has good stability in THF, acetonitrile and dimethylsulfoxide at low temperatures. Reactions with TABF are fast and can be carried out at room temperature or below. TABF is non-flammable (unlike DAST), easy to work-up, easy to handle and available at a low cost, thus making the overall process cost effective.

The compounds obtained by the processes of the present invention can be isolated and purified in a manner known in the art, for example by distilling off the solvent under vacuum and recrystallizing the residue obtained from a suitable solvent or subjecting it to one of the customary purification methods.

In general, suitable organic solvents include, but are not limited to, ethereal solvents, chlorinated solvents, aromatic solvents, alcoholic solvents, diethyl ether, 1,2-dimethoxyethane, tetrahydrofuran, diisopropyl ether and 1,4 dioxane. Suitable chlorinated solvents include, but are not limited to, dichloromethane, 1,2-dichloroethane, chloroform and carbon tetrachloride. Suitable aromatic solvents include, but are not limited to, benzene and toluene. Suitable alcoholic solvents include, but are not limited to, methanol, ethanol, n-propanol, isopropanol and tert-butanol. Suitable polar aprotic solvents include, but are not limited to, N,N-dimethylformamide and dimethyl sulfoxide.

The invention is explained in detail in the representative preparations given below which are provided by way of illustration only and therefore should not be construed to limit the scope of the invention.

PREPARATIONS AND EXAMPLES OF THE INVENTION

Preparation of (±)-2-N—BOC-Azabicyclo[2.2.1]heptan-3-one

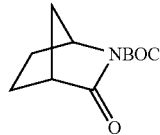

Step 1: (±)-2-N—BOC-Azabicyclo[2.2.1]hept-5-ene-3-one: A solution of di-tert-butyl dicarbonate (144 g, 660.5 mmol) in THF (100 ml) was added (20 min) to a stirred solution of (±)-2-azabicyclo[2.2.1]hept-5-ene-3-one (60 g, 549.8 mmol), triethylamine (83.5 g, 824.6 mmol) and 4-dimethylaminopyridine (6.7 g, 54.9 mmol) in THF (500 ml) at room temperature. The reaction mixture was stirred for another 2 h at room temperature. The solvent was evaporated under reduced pressure and the residue was diluted with EtOAc (800 ml) and washed with water (3×500 ml) and brine (400 ml). The EtOAc extract was dried ($Na_2SO_4$) and evaporated under reduced pressure to give 115 g of the compound as a white solid; $^1H$ NMR ($CDCl_3$, 300 MHz) δ 1.50 (s, 9H), 2.13-2.16 (m, 1H), 2.33-2.37 (m, 1H), 3.38-3.40 (m, 1H), 4.94-4.96 (m, 1H), 6.64-6.66 (m, 1H), 6.88-6.90 (m, 1H).

Step 2: (±)-2-N—BOC-Azabicyclo[2,2,1]heptan-3-one. To a solution of Step 1 intermediate (110 g, 525.90 mmol) in EtOAc (1100 ml) was added 5% Pd/C (5.05 g) and the mixture was maintained under hydrogen pressure (40 psi) for 2 h at room temperature. The catalyst was then filtered off and the filtrate was concentrated under reduced pressure to give 110 g of the compound as a white solid; $^1H$ NMR ($CDCl_3$, 300 MHz) δ 1.42 (d, J=10.2 Hz, 1H), 1.52 (s, 9H), 1.73-1.96 (m, 5H), 2.86 (brs, 1H), 4.53 (brs, 1H).

Preparation of (±)-(1SR,3RS)-3-N—BOC-Aminocyclopentylmethanol

A solution of (±)-2-N—BOC-Azabicyclo[2,2,1]heptan-3-one (109 g, 515.95 mmol) in methanol (1000 ml) was cooled to 10° C., and sodium borohydride (39 g, 1030 mmol) was added in lots over a period of 30 min. The mixture was stirred for 4 h at same temperature. The excess reagent was quenched with 1N HCl and the reaction mixture acidified to pH 5.0. Then methanol was removed under reduced pressure and the residue diluted with water (500 ml). The mixture was extracted with ethyl acetate (2×500 ml) and the combined organic extracts were washed with water (2×500 ml) followed by brine (500 ml). The solvent was evaporated under reduced pressure to give 102 g of the compound as a white solid; $^1$H NMR (CDCl$_3$, 300 MHz) δ 1.11-1.16 (m, 1H), 1.40-1.53 (m, 2H), 1.44 (s, 9H), 1.71-1.79 (m, 1H), 1.87-1.95 (m, 1H), 2.01-2.15 (m, 2H), 3.57 (t, J=5.1 Hz, 2H), 3.94 (brs, 1H), 4.73 (brs, 1H).

Preparation of (3SR,1RS)-3-(1H-1,2,4-Triazol-1-ylmethyl)cyclopentylamine (Method A)

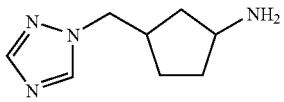

Step 1: cis-(±)-3-N—BOC-Aminocyclopentylmethyl-methanesulfonate: Methanesulfonyl chloride (63.9 g, 557.3 mmol) was added to a stirred and cooled (10° C.) solution of (±)-(1SR,3RS)-3-N—BOC-Aminocyclopentylmethanol (100 g, 464.4 mmol) and triethylamine (70.5 g, 696.7 mmol) in dry dichloromethane (1000 ml) under nitrogen atmosphere. The mixture was stirred at the same temperature for 30 min and then diluted with water (1000 ml). The organic and aqueous layers were separated. The aqueous layer was extracted with dichloromethane (500 ml) and the combined organic extracts were washed with water (2×1000 ml) and dried (Na$_2$SO$_4$). The solvent was evaporated under reduced pressure to give 135 g of the compound as a white solid; $^1$H NMR (CDCl$_3$, 300 MHz) δ 1.11-1.20 (m, 1H), 1.41-1.56 (m, 2H), 1.44 (s, 9H), 1.75-1.88 (m, 1H), 1.94-1.98 (m, 1H), 2.01-2.94 (m, 2H), 3.02 (s, 3H), 3.95 (brs, 1H), 4.15 (d, J=6.6 Hz, 2H), 4.53 (brs, 1H).

Step 2: N1-BOC-(3SR,1RS)-3-(1H-1,2,4-Triazol-1-ylmethyl)cyclopentylamine: A solution of 1H-1,2,4-triazole (45.8 g, 663.7 mmol) in DMA (300 ml) was added to a well-stirred suspension of 60% sodium hydride (23 g, 575.2 mmol) in DMA (500 ml) at RT and the mixture was stirred for 20 min under nitrogen atmosphere. A solution of Step 1 intermediate (130 g, 442.4 mmol) in DMA (500 ml) was added to the above mixture and heated at 80° C. for 8 h. The reaction mixture was cooled to room temperature and quenched with methanol (50 ml) then diluted with EtOAc (4000 ml) washed with water (3×4000 ml), brine (2000 ml) and dried (Na$_2$SO$_4$). The residue obtained after evaporation of the solvent was triturated with petroleum ether (1000 ml) to give 95 g of the product as a white solid; $^1$H NMR (CDCl$_3$, 300 MHz) δ 1.09-1.25 (m, 1H), 1.36-1.53 (m, 2H), 1.44 (m, 9H), 1.64-1.81 (m, 1H), 1.96-2.24 (m, 2H), 2.45-2.55 (m, 1H), 3.92 (m, 1H), 4.15 (d, J=7.2 Hz, 2H), 4.52 (brs, 1H) 7.93 (s, 1H), 8.05 (s, 1H).

Step 3: (3SR,1RS)-3-(1H-1,2,4-Triazol-1-ylmethyl)cyclopentylamine: A solution of 20% HCl in isopropyl alcohol (282 ml) was added to solution of Step 2 intermediate (94.0 g, 353.3 mmol) in IPA (658 ml) at 10° C. and the solution was maintained at room temperature for 2 h under a nitrogen atmosphere. Then excess of HCl and IPA was removed under reduced pressure. The hydrochloride salt obtained was dissolved in water (200 ml) and basified to pH 10 with solid K$_2$CO$_3$ and the solution was extracted with chloroform (5×100 ml). The combined organic layers were dried (Na$_2$SO$_4$) and concentrated under reduced pressure to give 51 g of the amine as a colorless oil; $^1$H NMR (CDCl$_3$, 300 MHz) δ 1.02-1.07 (m, 1H), 1.39-1.56 (m, 2H), 1.61 (br s, 2H), 1.64-1.80 (m, 1H), 1.82-1.90 (m, 1H), 1.97-2.05 (m, 1H), 2.49-2.55 (m, 1H), 3.37-3.42 (m, 1H), 4.16 (d, J=7.2 Hz, 2H), 7.91 (s, 1H), 8.03 (s, 1H).

Preparation of (3SR,1RS)-3-(1H-1,2,4-Triazol-1-ylmethyl)cyclopentylamine (Method B)

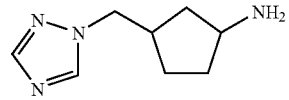

Step 1: To a stirred solution of (±)-(1SR,3RS)-3-N—BOC-Aminocyclopentylmethanol (30.0 g, 139.53 mmol), 1H-1,2,4-triazole (9.6 g, 139.13 mmol) and triphenylphosphine (40.26 g, 153.49 mmol) in dry THF (300 ml) was added diethyl azodicarboxylate (26.74 g, 153.40 mmol) under a nitrogen atmosphere and the mixture was heated at 60° C. for 1 h. The solvent was evaporated under reduced pressure to give a viscous residue which was dissolved in ethyl acetate (250 ml) and diluted with petroleum ether (600 ml) to result a white precipitate. The precipitated product was collected by filtration and washed with 20% EtOAc-petroleum ether to give 32 g of the product as a white solid, which showed identical spectral data to that of compound prepared by Method A.

Step 2: Deprotection of Step 1 intermediate (30 g) with 15% HCl in IPA followed by basic work-up as described above gave 17 g of the product as a colourless oil, which was identical in all respects with that obtained by Method A.

Preparation of (2S,4S)-4-Fluoropyrrolidine-2-carboxamide hydrochloride

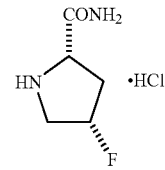

Step 1: tert-Butyl (2S,4S)-2-carbamoyl-4-fluoropyrrolidine-1-carboxylate: To a well stirred solution of (2S,4S)-1-

(tert-butoxycarbonyl)-4-fluoropyrrolidine-2-carboxylic acid (50 g, 0.2145 mmol) in dry THF (1000 ml) was added TEA (32.49 g, 0.3217 mmol) at room temperature. The mixture was cooled to −10° C. and ethyl chloroformate (34.93 g, 0.3217 mmol) was added over period of 20 min. The mixture was stirred for 30 min at the same temperature under nitrogen atmosphere and aqueous ammonium hydroxide (500 ml) was added. The aqueous mixture was stirred at room temperature for 18 h and THF in the mixture was evaporated under reduced pressure. The aqueous mixture was further diluted with water (100 ml) and extracted with chloroform (3×100 ml). The combined organic extracts were dried over $Na_2SO_4$ and concentrated under reduced pressure. The residue was stirred in petroleum ether (250 ml) for 20 min to give a white filterable solid. The product was collected by filtration and dried to give 44.7 g of the product as a white solid. $^1$H NMR (CDCl$_3$, 300 MHz) δ 1.48 (s, 9H), 2.20-2.80 (m, 2H), 3.51-3.85 (m, 2H), 4.38 (br s, 1H), 5.21 (d, J=52.2 Hz, 1H), 5.50 (br s, 1H), 6.16 (br s, 0.5H, rotomer), 6.59 (br s, 0.5H, rotomer)

Step 2: (2S,4S)-4-Fluoropyrrolidine-2-carboxamide hydrochloride: A solution of 12% HCl in ethyl acetate (100 ml) was added to solution of Step 1 intermediate (25 g, 116.68 mmol) in ethyl acetate (50 ml) and the mixture was maintained at room temperature for 1 h under a nitrogen atmosphere. The mixture was evaporated to dryness under reduced pressure to give 16 g of the hydrochloride salt as a white solid; $^1$H NMR (D$_2$O, 300 MHz) δ 1.54-2.88 (m, 2H), 3.56 (dd, J=13.2, 14.1 Hz, 1H), 3.79-3.90 (m, 1H), 4.64 (dd, J=3.0, 7.8 Hz, 1H), 5.48 (d, J=50.7 Hz, 1H), Preparation of (2S,4S)-4-fluoropyrrolidine-2-carbonitrile p-toluenesulfonate

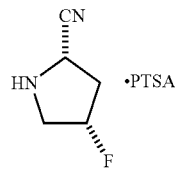

Step 1: tert-Butyl (2S,4S)-2-cyano-4-fluoropyrrolidine-1-carboxylate: To a stirred suspension of tert-butyl (2S,4S)-2-carbamoyl-4-fluoropyrrolidine-1-carboxylate (50 g, 0.2155 mmol) in dry dichloromethane (500 ml) was added triethylamine (87.06 g, 0.862 mmol) and the mixture was cooled to 0° C. Trifluoroacetic anhydride (58.83 g, 0.2801 mmol) was added over period of 10 min and the mixture was stirred for 30 min at same temperature under nitrogen atmosphere. The mixture was diluted with water (300 ml) and the layers were separated. The aqueous layer was extracted with dichloromethane (100 ml). The combined organic phase was washed with 1N HCl (200 ml), 5% aqueous NaHCO$_3$ (100 ml) and water (2×300 ml). The solution was dried over anhydrous Na$_2$SO$_4$ and then evaporated under reduced pressure to give 45 g of the product as a pale yellow solid; $^1$H NMR (CDCl$_3$, 300 MHz) δ 1.49-1.53 (d, 9H, rotomer), 2.25-2.47 (m, 1H), 2.64 (t, J=14.7 Hz, 1H), 3.52 (dd, J=9.6, 3.6 Hz, 0.5H, rotomer), 3.64 (dd, J=9.3, 3.3 Hz, 0.5H, rotomer), 3.73-3.94 (m, 1H), 4.64 (d, J=8.7 Hz, 0.6H, rotomer), 4.76 (d, J=8.7 Hz, 0.4H, rotomer), 5.31 (br d, J=51.3 Hz, 1H).

Step 2: (2S,4S)-2-Cyano-4-fluoropyrrolidine p-toluene sulfonate: To a stirred solution of Step 1 intermediate (40 g, 186.72 mmol) in acetonitrile (400 ml) was added p-toluene sulfonic acid (64.3 g, 373.33 mmol) and the solution was stirred at for 24 h at room temperature under nitrogen atmosphere. The solvent was evaporated under reduced pressure to afford a brown residue, which was triturated with petroleum ether (100 ml) to give a filterable solid. The solid was collected by filtration and dried to give 45 g of the product as an off-white solid; $^1$H NMR (CDCl$_3$, 300 MHz) δ 2.31 (s, 3H), 2.37-2.65 (m, 2H), 3.76-3.87 (m, 2H), 5.10 (br s, 2H), 5.33 (br d, J=51.6 Hz, 1H), 7.19 (d, J=8.1 Hz, 2H), 7.75 (d, J=8.1 Hz, 2H).

Preparation of (3S,1R)-3-(1H-1,2,4-Triazol-1-ylmethyl)cyclopententylamine

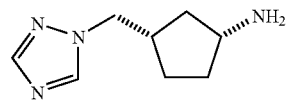

A solution of (−)-Dibenzoyl-L-tartaric acid (161.6 g, 451.2 mmol) in acetonitrile (485 ml) was added to a solution of (±)-(3SR,1RS)-3-(1H-1,2,4-triazol-1-ylmethyl)-cyclopentylamine (100 g, 601.6 mmol) in methanol (300 ml). The mixture was refluxed for 1 h, then cooled to room temperature and stirred for another 18 h. The diastereomeric salt separated out was collected by filtration. The salt was suspended in MeOH—CH$_3$CN mixture and refluxed for 1 h under stirring. The mixture was cooled to room temperature, further stirred for 4 h and the salt separated out was collected by filtration to give 105 g of the product as a white solid.

The above salt was dissolved in 5N K$_2$CO$_3$ (105 ml) and the mixture was extracted with chloroform (4×105 ml). The combined organic layers were dried (Na$_2$SO$_4$) and evaporated to give 33 g of the amine as a colorless oil; $^1$H NMR (CDCl$_3$, 300 MHz) δ 1.03-1.07 (m, 1H), 1.41-1.55 (m, 2H), 1.71-1.80 (m, 3H), 1.86-1.92 (m, 1H), 1.97-2.05 (m, 1H), 2.49-2.55 (m, 1H), 3.38-3.43 (m, 1H), 4.16 (d, J=7.2 Hz, 2H), 7.91 (s, 1H), 8.04 (s, 1H); [α]$_D$: −2.69° (c=0.5, MeOH); HPLC retention time: 15.8 min [Chiralpak AD-H, 250×4.6×5 μM; mobile phase: n-heptane:ethanol:diethylamine 70:30:0.01; detection at 210 nm]

Preparation of (3R,1S)-3-(1H-1,2,4-Triazol-1-ylmethyl)cyclopentylamine

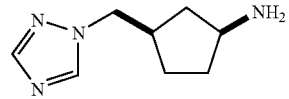

This enantiomer was prepared by resolution of (±)-(3SR,1RS)-3-(1H-1,2,4-triazol-1-ylmethyl)cyclopentylamine with (+)-Dibenzoyl-D-tartaric acid as described above to give 34 g of the product as colorless oil. $^1$H NMR (CDCl$_3$, 300 MHz) δ 1.03-1.69 (m, 1H), 1.41-1.56 (m, 2H), 1.72-1.80 (m, 3H), 1.85-1.91 (m, 1H), 1.98-2.06 (m, 1H), 2.50-2.55 (m, 1H), 3.37-3.43 (m, 1H), 4.17 (d, J=7.2 Hz, 2H), 7.92 (s, 1H), 8.04 (s, 1H); [α]$_D$+2.71° (c=0.5% in MeOH); HPLC retention time: 21.8 min [Chiralpak AD-H, 250×4.6×5 μM; mobile phase: n-heptane:ethanol:diethylamine 70:30:0.01; detection at 210 nm]

Preparation of Ethyl 2-[(3S,1R)-3-(1H-1,2,4-triazol-1-ylmethyl)-2-cyclopentylamino]-acetate

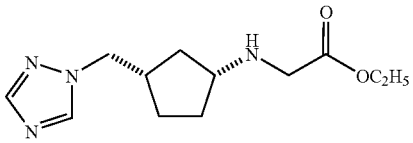

Step 1: Ethyl 2-[(1R,3S)-3-(1H-1,2,4-triazol-1-ylmethyl)cyclopentylimino]acetate: Anhydrous sodium sulfate (250 g) was added to a solution of (3S,1R)-3-(1H-1,2,4-triazol-1-ylmethyl)cyclopententylamine (50 g, 300.8 mmol) and 50% (w/v) ethyl glyoxalate in toluene (64 ml, 300.8 mmol) in dry dichloromethane (1000 ml) and the mixture was stirred at room temperature for 18 h under nitrogen atmosphere. Na$_2$SO$_4$ removed by filtration and the filtrate was evaporated under reduced pressure to give the crude product as an oil; $^1$H NMR (CDCl$_3$, 300 MHz) δ 1.31-1.38 (m, 3H), 1.42-1.56 (m, 1H), 1.64-1.73 (m, 1H), 1.80-1.99 (m, 4H), 2.64-2.75 (m, 1H), 3.81-3.87 (m, 1H), 4.21-4.36 (m, 4H), 7.66 (s, 1H), 7.94 (s, 1H), 8.10 (s, 1H).

Step 2: Ethyl 2-[(1R,3S)-3-(1H-1,2,4-triazol-1-ylmethyl)cyclopentylamino]acetate: The Step 1 intermediate in methanol (500 ml) was treated with Pd/C (5.0 g) under hydrogen atmosphere (50 psi) at room temperature for 3 h. The mixture was filtered to remove the catalyst and the filtrate was concentrated under reduced pressure to give 75 g of the product as a viscous liquid; $^1$H NMR (CDCl$_3$, 300 MHz) δ 1.18-1.30 (m, 4H), 1.48-1.62 (m, 2H), 1.68-1.84 (m, 1H), 1.86-1.90 (m, 1H), 1.96-2.05 (m, 1H), 3.16-3.20 (m, 1H), 3.39 (s, 2H), 4.16-4.27 (m, 5H), 7.93 (s, 1H), 8.09 (s, 1H).

Preparation of [(3S,1R)-3-(1H-1,2,4-Triazol-1-ylmethyl)cyclopentyl-N—BOC-amino]-acetic acid

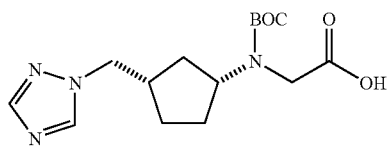

Method A:

Step 1: Ethyl 2-[(3S,1R)-3-(1H-1,2,4-triazol-1-ylmethyl)cyclopentyl-N—BOC-amino]acetate: To a solution of Ethyl 2-[(3S,1R)-3-(1H-1,2,4-triazol-1-ylmethyl)-2-cyclopentylamino]acetate (40.0 g, 158.53 mmol) and triethylamine (20.0 g, 198.16 mmol) in THF (200 ml) was added a solution of di-tert-butyl dicarbonate (38.0 g, 174.31 mmol) in THF (100 ml) at 0° C. The reaction mixture was allowed to stir at room temperature for 15 h. The mixture was concentrated and the residue obtained was dissolved in water and washed with ethyl acetate (2×100 ml). The aqueous layer was acidified to pH 4 with 1N HCl and extracted with dichloromethane (3×200 ml). The combined organic extracts were washed with water (100 ml), brine (100 ml) and dried over anhydrous sodium sulfate. The solvent was evaporated to give 52.0 g of the product as a liquid; $^1$H NMR (CDCl$_3$, 300 MHz) δ 1.25-1.37 (m, 3H), 1.42 (br s, 9H), 1.52-1.55 (m, 2H), 1.69-1.78 (m, 1H), 1.86-2.03 (m, 2H), 2.41-2.49 (m, 1H), 3.76 (br s, 2H), 4.08 (br s, 1H), 4.16-4.27 (m, 4H), 4.41-4.43 (m, 1H), 7.92 (s, 1H), 8.06 (s, 1H).

Step 2: [(3S,1R)-3-(1H-1,2,4-Triazol-1-ylmethyl)cyclopentyl-N—BOC-amino]acetic acid: To a solution of Step 1 intermediate (50.0 g, 141.87 mmol) in ethanol (250 ml) was added a solution of 1N sodium hydroxide solution (250 ml) at 0° C. The reaction mixture was allowed to stir at room temperature for 15 h. Most of the solvent was evaporated under reduced pressure and the residue was dissolved in water (250 ml) and washed with ethyl acetate (2×100 ml). The aqueous layer was acidified to pH 4 with 1N HCl and extracted with dichloromethane (3×200 ml). The combined organic layers were washed with water (100 ml), brine (100 ml) and dried (Na$_2$SO$_4$). The solvent was evaporated to give 40 g of the product as an off-white solid, $^1$H-NMR (CDCl$_3$, 300 MHz) δ 1.43 (brs, 9H), 1.61-1.72 (m, 2H), 1.75-1.83 (m, 1H), 1.92-1.94 (m, 2H), 2.42-2.52 (m, 1H), 3.83 (brs, 2H), 4.15-4.22 (m, 2H), 4.41 (brs, 2H), 6.00 (brs, 1H), 7.98 (s, 1H), 8.31 (s, 1H).

Method B:

To a solution of ethyl 2-[(3S,1R)-3-(1H-1,2,4-triazol-1-ylmethyl)-2-cyclopentylamino]acetate (75 g, 297.25 mmol) and di-tert-butyl dicarbonate (64.8 g, 297.5 mmol) in THF (750 ml) was added a solution of sodium hydroxide (29.72 g, 743.1 mmol) in water (250 ml) and the solution was stirred at room temperature for 8 h. The mixture was concentrated and the residue obtained was dissolved in water and washed with ethyl acetate (2×100 ml). The aqueous layer was acidified to pH 4 with 1N HCl and extracted with dichloromethane (4×200 ml). The combined organic extracts were washed with brine (300 ml) and dried over anhydrous sodium sulfate. The solvent was evaporated to give 77 g of the product as a white solid. Spectral data was this product identical with that of product isolated by Method A.

Preparation of Ethyl 2-[(3R,1S)-3-(1H-1,2,4-triazol-1-ylmethyl)-2-cyclopentylamino]-acetate

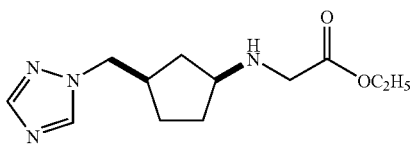

This compound was prepared from (3R,1S)-3-(1H-1,2,4-Triazol-1-ylmethyl)cyclopentylamine (50 g, 300.8 mmol) and 50% (w/v) ethyl glyoxalate in toluene (64 ml, 300.8 mmol) followed by hydrogenation as described in the preparation of ethyl 2-[(3S,1R)-3-(1H-1,2,4-triazol-1-ylmethyl)-2-cyclopentylamino]acetate to give 75 g of the product as a viscous liquid; $^1$H NMR (CDCl$_3$, 300 MHz) δ 1.17-1.29 (m, 4H), 1.48-1.59 (m, 2H), 1.67-1.84 (m, 1H), 1.72 (br s, 1H), 1.86-1.91 (m, 1H), 1.96-2.05 (m, 1H), 3.16-3.22 (m, 1H), 3.40 (s, 2H), 4.15-4.28 (m, 5H), 7.94 (s, 1H), 8.10 (s, 1H).

Preparation of [(3R,1S)-3-(1H-1,2,4-Triazol-1-ylm-ethyl)cyclopentyl-N—BOC-amino]-acetic acid

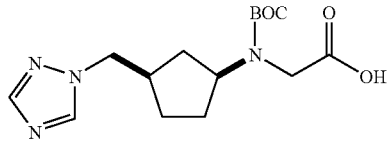

This compound was prepared from ethyl 2-[(3R,1S)-3-(1H-1,2,4-triazol-1-ylmethyl)-2-cyclopentylamino]acetate (75 g, 297.25 mmol) as described in the preparation of [(3S,1R)-3-(1H-1,2,4-Triazol-1-ylmethyl)cyclopentyl-N—BOC-amino]acetic acid (Method B) to give 77 g of the product as a white solid; $^1$H NMR (CDCl$_3$, 300 MHz) δ 1.44 (brs, 9H), 1.60-1.71 (m, 2H), 1.76-1.83 (m, 1H), 1.91-1.93 (m, 2H), 2.42-2.51 (m, 1H), 3.84 (brs, 2H), 4.16-4.22 (m, 2H), 4.42 (brs, 2H), 6.02 (brs, 1H), 7.98 (s, 1H), 8.32 (s, 1H).

Preparation of (2S,4S)-1-{2-[(3S,1R)-3-(1H-1,2,4-Triazol-1-ylmethyl)cyclopentyl-N—BOC-amino]acetyl}-4-fluoropyrrolidine-2-carboxamide

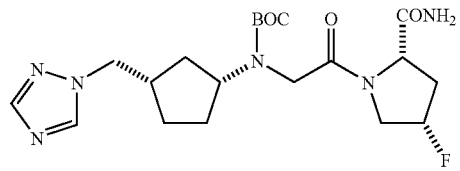

To a stirred and cooled (0° C.) mixture of [(3S,1R)-3-(1H-1,2,4-Triazol-1-ylmethyl)-cyclopentyl-N—BOC-amino]-acetic acid (10 g, 30.5 mmol) and 1-hydroxybenzotriazole (5 g, 36.9 mmol) in dichloromethane (200 ml) was added 1-(3-dimethylaminopropyl)-3-ethylcarbodiimide hydrochloride (7.1 g, 36.9 mmol) in portions and the mixture was stirred for 0.5 h at the same temperature to result a clear solution. A solution of (2S,4S)-4-fluoropyrrolidine-2-carboxamide p-toluenesulfonate (5.71 g, 33.9 mmol) and triethylamine (6.4 ml, 4.62 mmol) in dichloromethane (60 ml) was added and the mixture was stirred for 3 h at room temperature. The reaction mixture was diluted with DCM (100 ml) and water (200 ml) and the layers were separated. The organic layer was washed with 0.5N HCl (100 ml) and then with brine (50 ml). The solvent was evaporated under reduced pressure to give 10 g of the product as a white solid; $^1$H NMR (300 MHz, CDCl$_3$) δ 1.25-1.33 (m, 2H), 1.42 (s, 9H), 1.70-1.99 (m, 5H), 2.04-2.47 (m, 2H), 2.80-2.82 (m, 1H), 3.63-3.91 (m, 4H), 4.14-4.17 (m, 2H), 4.35-4.37 (m, 2H), 4.74 (d, J=9.6 Hz, 1H), 5.25-5.42 (m, 1H), 7.93 (s, 1H), 8.06 (s, 0.6H, rotomer), 8.08 (s, 0.4H, rotomer).

Preparation of (2S,4S)-1-{2-[(3S,1R)-3-(1H-1,2,4-Triazol-1-ylmethyl)cyclopentyl-N—BOC-amino]acetyl}-4-fluoropyrrolidine-2-carbonitrile

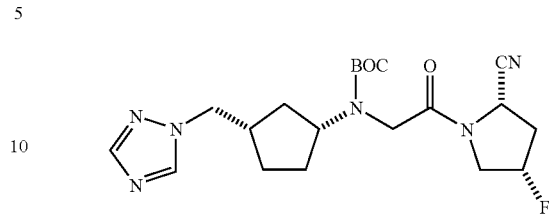

Method A:

Trifluoroacetic anhydride (7.2 g, 34.28 mmol) was added to a stirred and cooled (0° C.) solution of (2S,4S)-1-{2-[(3S,1R)-3-(1H-1,2,4-triazol-1-ylmethyl)cyclopentyl-N—BOC-amino]acetyl}-4-fluoropyrrolidine-2-carboxamide (10.0 g, 22.91 mmol) and triethylamine (7.0 g, 69.30 mmol) in dry dichloromethane (100 ml) and stirred at the same temperature for 20 minutes. The mixture was diluted with water (100 ml) and the layers were separated. The organic layer was separated and washed with water (2×100 ml) and dried over anhydrous sodium sulfate. The solvent was evaporated under reduced pressure to give 8.9 g of the product as a white solid; $^1$H NMR (300 MHz, CDCl$_3$) δ 1.22-1.37 (m, 2H), 1.43 (s, 9H), 1.61-1.81 (m, 2H), 1.87-2.03 (m, 3H), 2.21-2.27 (m, 1H), 2.34-2.50 (m, 1H), 2.62-2.76 (m, 1H), 3.69-4.01 (m, 3H), 4.13-4.23 (m, 3H), 4.97 (d, J=9.3 Hz, 1H), 5.35 (d, J=51.6 Hz, 0.3H, rotomer), 5.45 (d, J=51.0 Hz, 0.7H. rotomer), 7.93 (s, 1H), 8.07 (s, 0.4H, rotomer), 8.11 (s, 0.6H, rotomer).

Method B:

Triethylamine (54.6 g, 539.50 mmol) was added to a mixture of [(3S,1R)-3-(1H-1,2,4-Triazol-1-ylmethyl)cyclopentyl-N—BOC-amino]acetic acid (50 g, 154.14 mmol) and 1-hydroxybenzotriazole (25 g, 184.97 mmol), 1-(3-dimethylaminopropyl)-3-ethylcarbodiimide hydrochloride (35 g, 184.97 mmol) and (2S,4S)-4-fluoropyrrolidine-2-carbonitrile hydrochloride (27 g, 184.97 mmol) in dry dichloromethane (500 ml). The mixture was stirred at room temperature for 18 h. The mixture was washed with water (2×300 ml), brine (100 ml) and dried. The solvent was evaporated under reduced pressure to give 61.3 g of the product as a white solid, which showed identical spectral data as given in Method A.

Method C:

To a stirred and cooled (0° C.) mixture of [(3S,1R)-3-(1H-1,2,4-Triazol-1-ylmethyl)cyclopentyl-N—BOC-amino]acetic acid (50 g, 154.14 mmol) and triethylamine (18.68 g, 184.96 mmol) in THF (400 ml), was added ethyl chloroformate (20.07 g, 184.96 mmol). The mixture was stirred for 30 min at same temperature under a nitrogen atmosphere. A solution of (2S,4S)-4-fluoropyrrolidine-2-carbonitrile p-toluenesulfonate (52.96 g, 184.96 mmol) and triethylamine (18.68 g, 184.96 mmol) in 30% aqueous tetrahydrofuran (150 ml) was added and mixture was further stirred at room temperature for 18 h. The solvent was evaporated under reduced pressure and the residue obtained was dissolved in chloroform (500 ml). The chloroform solution was washed with water (500 ml) and brine (250 ml). The solvent was evaporated under reduced pressure to give 60.9 g of the product as a white solid, which showed identical spectral data as given in Method A.

Preparation of (2S,4S)-1-{2-[(3R,1S)-3-(1H-1,2,4-Triazol-1-ylmethyl)cyclopentyl-N—BOC-amino]acetyl}-4-fluoropyrrolidine-2-carbonitrile

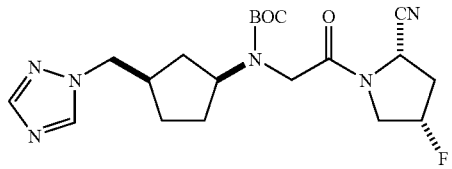

This compound was prepared from [(3R,1S)-3-(1H-1,2,4-Triazol-1-ylmethyl)cyclopentyl-N—BOC-amino]acetic acid (50 g, 154.14 mmol) and (2S,4S)-4-fluoropyrrolidine-2-carbonitrile p-toluenesulfonate (52.96 g, 184.96 mmol) as described in the preparation of its enantiomer (Method C) to give 59.9 g of the product as a white solid; $^1$H NMR (300 MHz, CDCl$_3$) δ 1.22-1.36 (m, 2H), 1.44 (s, 9H), 1.62-1.81 (m, 2H), 1.88-2.04 (m, 3H), 2.22-2.27 (m, 1H), 2.34-2.49 (m, 1H), 2.62-2.77 (m, 1H), 3.69-4.01 (m, 3H), 4.13-4.23 (m, 3H), 4.99 (d, J=9.3 Hz, 1H), 5.33 (d, J=51.7 Hz, 0.3H, rotomer), 5.45 (d, J=51.0 Hz, 0.7H. rotomer), 7.92 (s, 1H), 8.08 (s, 0.4H, rotomer), 8.10 (s, 0.6H, rotomer).

Preparation of (2S,4S)-1-{2-[(3S,1R)-3-(1H-1,2,4-Triazol-1-ylmethyl)cyclopentylamino]-acetyl}-4-fluoropyrrolidine-2-carbonitrile

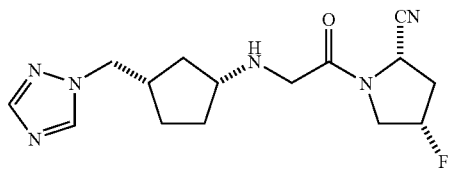

To a stirred solution of (2S,4S)-1-{2-[(3S,1R)-3-(1H-1,2,4-Triazol-1-ylmethyl)cyclopentyl-N—BOC-amino]acetyl}-4-fluoropyrrolidine-2-carbonitrile (50 g, 118.91 mmol) in EtOAc (50 ml) was added 12% HCl in EtOAc (250 ml) at 10° C. The mixture was stirred for 1 h at same temperature. The excess of HCl and EtOAc was distilled out under reduced pressure to give 40 g of a hydrochloride salt as hygrospic solid. The salt was dissolved in water (80 ml) and the pH of the solution was adjusted to 13 with solid K$_2$CO$_3$. The product was extracted with chloroform (5×100 ml). The combined organic layer was dried (K$_2$CO$_3$) and evaporated under reduce pressure to give a viscous residue. The residue was dissolved EtOAc (50 ml) and stirred for 20 min and the solid precipitated out was collected by filtration to give 32 g of the product as a white solid; IR (KBr) 3316, 2947, 2242, 1662, 1416, 1140 cm$^{-1}$; $^1$H NMR (300 MHz, CDCl$_3$) δ 1.09-1.20 (m, 1H), 1.44-1.60 (m, 2H), 1.70-2.08 (m, 4H), 2.21-2.42 (m, 1H), 2.46-2.76 (m, 2H), 3.11-3.20 (m, 1H), 3.36 (d, J=4.8 Hz, 1.6H, rotomer), 3.30-4.06 (m, 2.4H, rotomer), 4.16 (d, J=7.5 Hz, 2H), 4.95 (d, J=9.3 Hz, 1H), 5.36 (dt, J=4.0, 51.3 Hz, 0.24H, rotomer), 5.43 (dt, J=3.9, 50.7 Hz, 0.76H, rotomer), 7.93 (s, 1H), 8.06 (s, 1H).

Preparation of (2S,4S)-1-{2-[(3R,1S)-3-(1H-1,2,4-Triazol-1-ylmethyl)cyclopentyl-amino]acetyl}-4-fluoropyrrolidine-2-carbonitrile

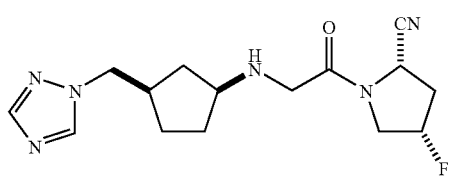

This compound was prepared from (2S,4S)-1-{2-[(3R,1S)-3-(1H-1,2,4-triazol-1-ylmethyl)cyclopentyl-N—BOC-amino]acetyl}-4-fluoropyrrolidine-2-carbonitrile (50 g, 118.91 mmol) as described in the preparation of its enantiomer to give 31.2 g of the product as a white solid; IR (KBr) 3328, 3118, 2948, 2239, 1656, 1510, 1327, 1267, 1074, 1016 cm$^{-1}$; $^1$H NMR (CDCl$_3$, 300 MHz) δ 1.10-1.25 (m, 1H), 1.47-1.59 (m, 2H), 1.71-2.05 (m, 4H), 2.20-2.40 (m, 1H), 2.46-2.74 (m, 2H), 3.12-3.19 (m, 1H), 3.36 (d, J=9.3 Hz, rotomer, 1.5H), 3.30-4.13 (m, rotomer, 2.5H), 4.17 (d, J=7.2 Hz, 2H), 4.95 (d, J=9.0 Hz, 1H), 5.36 (dt, J=50.0, 4.0 Hz, rotomer, 0.25H), 5.43 (dt, J=51.3, 3.3 Hz, rotomer, 0.75 Hz), 7.93 (s, 1H), 8.06 (s, 1H)

Preparation of (2S,4S)-1-{2-[(3S,1R)-3-(1H-1,2,4-Triazol-1-ylmethyl)cyclopentylamino]-acetyl}-4-fluoropyrrolidine-2-carbonitrile methanesulfonate

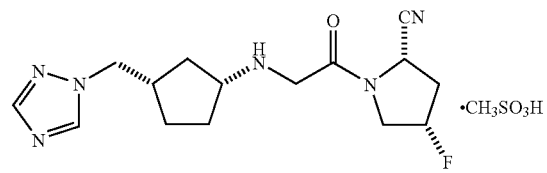

To a stirred solution of (2S,4S)-1-{2-[(3S,1R)-3S,1R)-3-(1H-1,2,4-Triazol-1-ylmethyl)cyclopentylamino]acetyl}-4-fluoropyrrolidine-2-carbonitrile (50 g, 156.07 mmol) in acetonitile (200 ml) was and added methanesulfonic acid (25 g, 260.14 mmol) to result a clear solution. The solution was stirred for 8 h under nitrogen atmosphere and the product separated out was collected by filtration. The residue was washed with ice-cold acetonitile (2×50 ml) and dried under vacuum to give 61.2 g of the methanesulfonate salt as a white solid; IR (KBr) 3430, 2964, 2248, 1673, 1513, 1428, 1340, 1208, 1058 cm$^{-1}$; $^1$H NMR (300 MHz, D$_2$O) δ 1.32-1.56 (m, 2H), 1.70-1.81 (m, 2H), 2.05-2.26 (m, 2H), 2.35-2.67 (m, 3H), 2.73 (s, 3H), 3.60-4.19 (m, 5H), 4.25 (d, J=7.2 Hz, 2H), 5.00 (d, J=9.9 Hz, 0.9H, rotomer), 5.11 (d, J=8.4 Hz, 0.1H, rotomer), 5.45 (d, J=50.7 Hz, 0.1 Hz, rotomer), 5.49 (d, J=50.7 Hz, 0.9H, rotomer), 8.00 (s, 1H), 8.41 (s, 1H).

Preparation of (2S,4S)-1-{2-[(3S,1R)-3-(1H-1,2,4-Triazol-1-ylmethyl)cyclopentylamino]-acetyl}-4-fluoropyrrolidine-2-carbonitrile p-toluene sulfonate

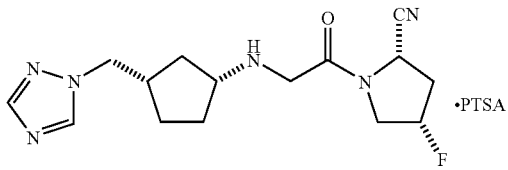

To a solution of (2S,4S)-1-{2-[(3S,1R)-3-(1H-1,2,4-Triazol-1-ylmethyl)cyclopentyl-amino]acetyl}-4-fluoropyrrolidine-2-carbonitrile (50 g, 156.07 mmol) in acetonitrile (250 ml) was added p-toluenesulfonic acid (47 g, 272.93 mmol) at room temperature under nitrogen atmosphere to result a clear solution. The solution was further stirred for 18 h and the solvent was evaporated under reduced pressure to result a viscous residue. The residue was stirred in dry acetone (200 ml) for 1 h to result a white solid, which was collected by filtration. The residue was washed with acetone (2×50 ml) and dried under vacuum to give 72.6 g of the salt as a white solid; $^1$H NMR (300 MHz, D$_2$O) δ 1.28-1.50 (m, 2H), 1.68-1.77 (m, 2H), 1.99-2.19 (m, 2H), 2.27-2.69 (m, 3H), 2.38 (s, 3H), 3.53-3.63 (m, 2H), 3.72-4.11 (m, 3H), 4.18 (d, J=7.2 Hz, 2H), 4.95 (d, J=9.3 Hz, 1H), 5.45 (d, J=50.7 Hz, 1H), 7.45 (d, J=6.3 Hz, 2H), 7.71 (d, J=6.3 Hz, 2H), 7.96 (s, 1H), 8.34 (s, 1H).

Preparation of tert-Butyl (2S,4R)-2-(aminocarbonyl)-4-hydroxypyrrolidine-1-carboxylate To a 5 L 4-necked RB flask, fitted with a mechanical stirrer and condenser, tetrahydrofuran (1875 ml) and (2S,4R)-4-hydroxypyrrolidine-2-carboxamide (187.5 g, 1.44 M) were added at a temperature of about 25-35° C. while stirring. The reaction mixture was cooled to 0-5° C. and maintained for 30 min while stirring. Triethylamine (291.5 g, 2.88M) was added to reaction mixture at 0-5° C. over a period of 10-15 min. The reaction mixture was stirred for 10-15 min. BOC-anhydride (377.3 g, 1.73M) was charged very slowly for 10-15 min at 0-5° C. The reaction mass was stirred at 25-30° C. for 5-6 hrs. The completion of the reaction was monitored on TLC. Subsequently, the reaction mass was filtered through a celite bed, and the celite cake was washed with hot ethyl acetate (852.0 ml) thrice. The ethyl acetate was distilled off under vacuum at 45-50° C. To the crude product obtained after distillation was added toluene (852.0 ml), and the mixture was stirred for an additional 30 min at reaction temperature. The slurry mass was filtered and the cake was washed with hexane (1.705 L) to get a white solid. The product was dried under vacuum at 45-50° C. until the moisture content reached <1%. The dried product appeared as an off white to pale yellow solid (weight 301.5 g, yield 88-94%, purity 97-98% by HPLC).

Preparation of tert-Butyl(2S,4R)-2-(aminocarbonyl)-4-benzoyloxy-pyrroloidine-1-carboxylate In a 5 L 4-necked RB Flask, fitted with a mechanical stirrer and reflux condenser, methylene dichloride (MDC) (3000 ml) and tert-Butyl (2S,4R)-2-(aminocarbonyl)-4-hydroxypyrrolidine-1-carboxylate (300 g, 1.30M) were added and stirred for 10 min. Pyridine (215.0 ml) was charged slowly over a period of 10-15 min and maintained for a further 10-15 min. The reaction mass was cooled to 0-5° C. Benzoyl chloride (275 g, 1.95M) was charged very slowly over a period of 25-30 min. Cooling was removed and the reaction mass was stirred for 4-5 hrs at 25-30° C. The reaction was monitored by TLC. After completion of the reaction, the reaction mass was quenched into ice water. The reaction mass was stirred for 20-30 min. The lower organic layer was separated. MDC (1250 ml) was added again to the aqueous layer and the mixture was stirred for 20 min. The lower organic layer was separated and the extraction with MDC (1000 ml) was repeated. All organic layers were combined and water (1000 ml) was added. The mixture was stirred for 20 min. The lower organic layer was separated. The organic layer was dried over sodium sulfate (10 g). The MDC layer (95%) was distilled off at 40-45° C. After distillation, diisopropyl ether (1500 ml) was added and the mixture was stirred for a further 20 min at 25-30° C. The solid precipitate was filtered and washed with diisopropyl ether (400 ml). The product was dried at 40-45° C. under vacuum until LOD reached <1%. The dried product appeared as an off white to pale yellow powder (weight 376.5 g, yield 85-90%, purity 90-95% by HPLC).

Preparation of tert-Butyl(2S,4R)-2-cyano-4-benzoyloxy pyrrolidine-1-carboxylate

In a 5 L 4-necked RB flask fitted with a mechanical stirrer and condenser, pyridine (3750 ml) and imidazole (152.5 g, 2.24M) were added at 25-30° C. and the reaction was cooled to −5-0° C. tert-Butyl(2S,4R)-2-(aminocarbonyl)-4-benzoyloxy-pyrrolidine-1-carboxylate (375 g, 1.12M) was added and the reaction was maintained at −5-0° C. for 25-30 min. POCl$_3$ (687 g, 4.49M) was added very slowly into the reaction mass over a period of 30 min. The reaction was maintained further for 45-60 min. at −5-0° C. The reaction was monitored by TLC. After completion, the reaction mass was quenched in an ice (300 g) and salt (50 g) mixture. Ethyl acetate (5000 ml) was added to the reaction mass, followed by water (2500 ml). The reaction mass was stirred for 30 min. The upper organic layer was separated. Ethyl acetate (2500 ml) was added to the aqueous layer and stirred for 20 min. The upper organic layer was separated and the ethyl acetate extraction was repeated. All organic layers were combined, to which a 5% HCl (2500 ml) solution was added and stirred for 20 min. The HCl washing was repeated thrice. The upper organic layer was separated. To the ethyl acetate layer was added a saturated sodium bicarbonate (375 g) solution, and the mixture stirred for 20 min. The organic layer was separated and dried over sodium sulphate (200 g). The ethyl acetate (95%) was distilled off at 45-50° C. under vacuum. After completion of distillation diisopropyl ether (2500 ml) was added, and the mixture was stirred at 0-5° C. for 30 min. The crude product was filtered to give a pale yellow solid, and the solid was washed with prechilled diisopropyl ether (500 ml) and sucked dry. The product was dried at 45-50° C. under vacuum until LOD reached <1%. The dried product appeared as a pale yellow to yellow powder (weight 242.75 g, yield 65-70%, purity 90-95% by HPLC).

Preparation of tert-Butyl(2S,4R)-2-cyano-4-hydroxy-pyrrolidine-1-carboxylate

In a 5 L 4-necked RB flask fitted with a mechanical stirrer and condenser, methanol (2500 ml) was added and the reaction mass was cooled to 0-5° C. by external cooling. Ammonia gas was purged into the methanol for 2-3 hrs. The ammonia content in the methanol was about 15-20%. tert-Butyl (2S,4R)-2-cyano-4-benzoyloxy-pyrrolidine-1-carboxylate (241.25 g, 0.76M) was added to the reaction mass. The reaction was maintained for 2-3 hrs at 5-10° C. and monitored by TLC. After completion of the reaction, the methanol was distilled off at 45-50° C. under vacuum. The obtained residue was cooled to 0-5° C. and diisopropyl ether (1250 ml) was added at 0-5° C. The reaction mass was maintained for 30 min. The obtained product was filtered and washed with diisopropyl ether (500 ml). The product was dried at 45-50° C. under vacuum until LOD reached <0.5%. The dried product appeared as an off white to white crystalline powder (weight 87.75 g, yield 50-58%, purity 85-90% by HPLC).

Preparation of tert-Butyl (2S,4S)-2-cyano-4-fluoro-1-pyrrolidine-1-carboxylate

In a 3 L 4-necked RB flask, fitted with a mechanical stirrer and condenser, MDC (880.0 ml) was added and stirring begun. tert-Butyl (2S,4R)-2-cyano-4-hydroxy-pyrrolidine-1-carboxylate (86.25 g, 0.406M) was added and the reaction mass was maintained at 20-25° C. for 30 min. The reaction mass was cooled to −25 to −20° C. by external cooling using dry ice. Diethyl amino sulphurtrifluoride (98.5 g, 0.611M) was added in one lot at −15 to −20° C. The reaction mass was maintained at 25-30° C. for 24-26 hrs. The reaction was monitored by TLC. After completion of the reaction, the reaction mass was quenched in a chilled saturated sodium bicarbonate (125 g in 1250 ml of water) solution. The aqueous layer was extracted with MDC (1850 ml) twice. The organic layer was washed with water followed by a brine solution. The MDC layer was dried over sodium sulphate (10 g). The MDC was distilled off at 40-45° C. The obtained residue was cooled to 0-5° C. Diisopropyl ether (500 ml) was added at 0-5° C. and the reaction mass was maintained for 30 min. The obtained product was filtered and washed with diisopropyl ether (200 ml), and the product was sucked dry. The product was dried at 45-50° C. under vacuum until LOD reached <1%. The dried product appeared as a yellow to light brown powder (weight 70.25 g, yield 70-75%, purity 90-95% by HPLC).

Preparation of (2S,4S)-1-(chloroacetyl)-4-fluoropyrrolidine-2-carbonitrile

In a 2L 4-necked RB flask, filled with a mechanical stirrer and condenser, acetonitrile (687.5 ml) was added and stirring begun. Tert-Butyl (2S,4S)-2-cyano-4-fluoro-1-pyrrolidine-1-carboxylate (68.75 g, 0.321M) was added at a temperature of about 25-35° C. while stirring. The reaction was cooled to 0-5° C. p-toluene sulphonic acid (122 g, 0.64M) was added in one lot at 0-5° C. The temperature of the reaction mass was slowly increased to 40-45° C. The reaction mixture was stirred for 3 hrs at 40-45° C. The reaction was monitored by TLC. After completion of the reaction, the mass was cooled to 0-5° C. Tri ethyl amine (112 ml) was added into the reaction mass followed by chloro acetyl chloride (43.5 g, 0.38M) at 0-5° C. The reaction was maintained at 0-5° C. and stirred for 45-60 min. The reaction was monitored by TLC. After completion of the reaction, the reaction mass was diluted with MDC (2500 ml). The reaction mass was quenched in a saturated sodium bicarbonate (2500 ml) solution and stirred for 30 min. The lower organic layer was separated. The aqueous layer was extracted with additional MDC (1.25 L). The MDC layer was washed with water followed by a brine solution. The MDC layer was dried over sodium sulphate (100 g). The MDC layer was distilled off at 40-45° C. After concentration, ethanol (250 ml) was added and the reaction mass was stirred for 30 min. The reaction mass was filtered and washed with ethanol (100 ml), and the product was sucked dry. The product was dried at 45-50° C. under vacuum until LOD reached <1%. The dried product appeared as a light brown crystalline powder (weight 46.25 g, yield 75-80%, purity 98-99.5% by HPLC).

Preparation of 1-tert-butyl(2S,4R) 2-methyl 4-[(methylsulfonyl)oxy]pyrrolidine-1,2-dicarboxylate In a 1.0 L 4-necked RB flask fitted with a mechanical stirrer and a reflux condenser and under a nitrogen blanket, 1-tert-butyl(2S,4R) 2-methyl 4-hydroxypyrrolidine-1,2-dicarboxylate (100 gm) and dichloromethane (1000 ml) were added at a temperature 25-35° C. while stirring. The reaction mixture was cooled to 0-5° C. and triethyl amine (18.2 g, 0.180M) was added. The reaction temperature was maintained for 15 min and then methane sulfonyl chloride (16.6 g, 0.145M) was added dropwise at 0-5° C. while stirring. The reaction mixture was maintained for 3-4 hr at 0-5° C. The reaction was monitored by TLC. After ascertaining the completion of the reaction, water (168 ml) was added while stirring and the layers were separated. One more dichloromethane (600 ml) extraction was given to aqueous layer. Two water washings were given to the MDC layer. The dichloromethane layer was dried over anhydrous sodium sulphate. The MDC layer (95%) was concentrated under vacuum below 45° C. After distillation n-hexane (600 ml) was added and the mixture stirred for 20 min at 0-5° C. The solid precipitate was filtered and the product was washed with hexane (200 ml). The product was dried at 40-45° C. under vacuum.

Preparation of 1-tert-butyl(2S,4R) 2-(aminocarbonyl)-4-[(methylsulfonyl)oxy]pyrrolidine-1-carboxylate In a 2.0 L autoclave, 1-tert-butyl 2-methyl 4-[(methylsulfonyl) oxy]pyrrolidine-1,2-dicarboxylate (100 g, 0.309M) and methanol (1.0 L) were added at 25-35° C. while stirring. The ammonia gas was purged into the reaction mixture at a pressure of 5-6 kg/cm$^2$ for 12-14 hrs. The progress of the reaction was monitored by TLC. After completion, the methanol was distilled below 50° C. under vacuum. Hexane (500 ml) was added to the resulting mass and the trace methanol was distilled off. The residue was diluted with water (500 ml) and the precipitated product was filtered. The product cake was washed with DM water (100 ml×2) and dried. The dried product appeared as a white color solid (weight about 80-84 g, yield 91-92%, m.p. 166-168° C., purity 98% by HPLC). The IR (KBr) spectrum showed peaks at 3450 (NH str), 3180 (CH str), and 1670 (CONH str) cm-1. The 1H NMR (DMSO-d6) showed δ 11 (s, 1H), 9.0 (s, 1H), 8.2 (s, 2H), 7.6-7.7 (m, 1H), and 7.3-7.4 (m, 3H). The CI mass showed m/z 438 (M+). Elemental analysis calculated 52.08% C, 2.53% H, and 9.59% N. Observed was 52.0% C, 2.30% H, and 9.86% N.

Preparation of 1-tert-butyl(2S,4S) 2-(aminocarbonyl)-4-fluoropyrrolidine-1-carboxylate In a 5.0 L 4-necked RB flask, fitted with a mechanical stirrer and reflux condenser, were added tert-butyl 2-(aminocarbonyl)-4-[(methylsulfonyl)oxy]pyrrolidine-1-carboxylate (100 gm, 0.32 M), THF (500 ml), a tetrabutylammonium fluoride solution (153.4 gm, 0.48 mol in 500 ml THF) and water (35 ml) at 25-35° C. while stirring. The reaction mixture was brought to 55-60° C. and maintained for 48-60 hrs while stirring. The progress of the reaction was monitored by HPLC and after ascertaining completion, the reaction mixture was poured slowly into an ice cold water (1.5 L) and dichloromethane (0.72 L) mixture. The aqueous layer was washed with additional MDC (210 ml×3). The organic layers were combined and washed with a saturated brine solution (0.5 L). The dichloromethane layer was distilled below 40° C. under vacuum and hexane (500 ml) was added to the resulting mass. The trace dichloromethane was distilled off. The resulting mass was taken as such to the next stage.

Preparation of 1-tert-butyl (2S,4S)-2-cyano-4-fluoropyrrolidine-1-carboxylate

In a 5.0 L 4-necked RB flask, fitted with a mechanical stirrer and reflux condenser, pyridine (1000 ml) and imidazole (58.6 gm, 0.86 mol) were added at 25-35° C. while stirring. The reaction mixture was cooled to 0-5° C. while stirring for 30 min, tert-butyl 2-(aminocarbonyl)-4-fluoropyrrolidine-1-carboxylate (100 gm, 0.43 mol) and phosphorous oxychloride (165.7 gm, 1.07 mol) were added slowly at 0-5° C. while stirring. After addition, the reaction mixture was maintained for 1 hr. The progress of the reaction was monitored by TLC. After ascertaining completion of the reaction by TLC, the reaction mixture was poured into an ice cold water (5 L), sodium chloride and ethylacetate (800 ml) mixture. The aqueous layer was washed with an ethyl acetate (800 ml), dilute HCl (4 100), sodium bicarbonate and saturated brine solution. The ethylacetate layer was distilled below 55° C. under vacuum and hexane (500 ml) was added to the resulting mass. Trace ethylacetate was distilled off. The resulting mass was taken as such to the next stage.

Preparation of (2S,4S)-1-(chloroacetyl)-4-fluoropyrrolidine-2-carbonitrile

In a 2 L 4-necked RB flask, filled with a mechanical stirrer and condenser, acetonitrile (1000 ml) was added and stirring was begun. tert-butyl (2S,4S)-2-cyano-4-fluoro-1-pyrrolidine-1-carboxylate (100 gm, 0.46 M) was added at 25-35° C. while stirring. The reaction was cooled to 0-5° C. p-toluene sulphonic acid (177.5 g, 0.93 M) was added in one lot at 0-5° C. The temperature of the reaction mass was slowly increased to 40-45° C. The reaction mixture was stirred for 3 hrs at 40-45° C. The reaction was monitored by TLC. After completion of the reaction; the mass was cooled to 0-5° C. Triethylamine (163.8 ml, 1.16 mol) was added to the reaction mass, followed by chloroacetyl chloride (63.365 g, 0.56 M) at 0-5° C. The reaction was maintained at 0-5° C. and stirred for 45-60 min. The reaction was monitored by TLC. After completion of the reaction, the reaction mass was diluted with MDC (3000 ml). The reaction mass was quenched in a saturated sodium bicarbonate (3500 ml) solution and stirred for 30 min. The lower organic layer was separated. The aqueous layer was extracted with additional MDC (1.25 L). The MDC layer was washed with water followed by a brine solution. The MDC layer was dried over sodium sulphate (100 g) and distilled off at 40-45° C. After concentration, chloroform (150 ml) was added and the reaction mass was stirred for 30 min. The reaction mass was filtered and washed with chloroform (100 ml), and the product was sucked dry. The product was dried at 45-50° C. under vacuum until LOD reached <1%. The dried product appeared as a light pink crystalline powder (weight about 19.5-20 gm, yield 19-20%, HPLC purity 97%, M.P 140-142° C., SOR (1% methanol)-121-124°). The 1H-NMR (CDCl$_3$) showed δ 5.5-5.29 (m, 1H), 5.08-4.39 (m, 1H), 4.06 (s, 2H), 4.2-3.81 (m, 2H), and 2.8-2.01 (m, 2H). The C.I mass showed m/Z 191 (M+).

Although the invention herein has been described with reference to particular embodiments, these embodiments are merely illustrative of the principles and applications of the present invention. Therefore, numerous modifications may be made to the illustrative embodiments and other arrangements may be devised without departing from the spirit and scope of the present invention as described above. All publications and patent applications cited in this application are herein incorporated by reference to the same extent as if each individual publication or patent application was specifically and individually indicated to be incorporated herein by reference.

We claim:

1. A compound selected from

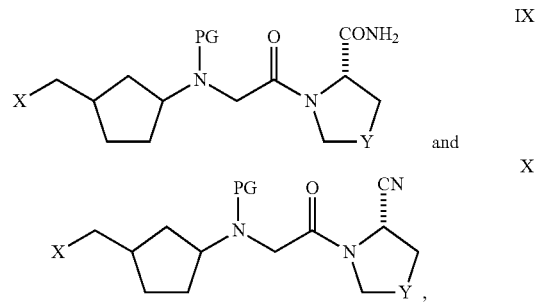

and or a stereoisomer thereof, wherein X is a substituted or unsubstituted cycloalkyl, substituted or unsubstituted cycloalkenyl, substituted or unsubstituted aryl, substituted or unsubstituted aralkyl, substituted or unsubstituted heteroaryl, substituted or unsubstituted heterocyclic ring, substituted or unsubstituted heterocyclylalkyl, or substituted or unsubstituted heteroarylalkyl, Y is CH$_2$ or CHF, and PG is a suitable nitrogen protecting group.

2. The compound of claim 1, wherein X is substituted or unsubstituted heteroaryl, or substituted or unsubstituted heterocyclic ring containing at least one nitrogen.

3. The compound of claim 2, wherein X is 5-membered heteroaryl ring containing at least one nitrogen atom.

4. The compound of claim 1, wherein PG is selected from acetyl, trifluoroacetyl, t-butyloxycarbonyl (BOC), benzyloxycarbonyl (CBz), 9-fluorenylmethylenoxycarbonyl (Fmoc), benzyl, and optionally substituted benzyl.

5. The compound of claim 4, wherein PG is t-butyloxycarbonyl (BOC) or benzyloxycarbonyl.

6. The compound of claim 1, wherein X is triazolyl.

7. A pharmaceutical composition comprising:
(a) a compound of the formula

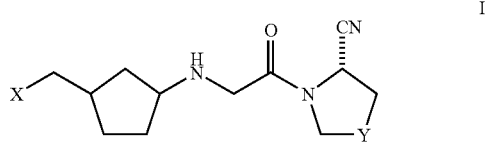

or a pharmaceutically acceptable salt thereof, or a stereoisomer thereof, wherein X is a substituted or unsubstituted cycloalkyl, substituted or unsubstituted cycloalkenyl, substituted or unsubstituted aryl, substituted or unsubstituted aralkyl, substituted or unsubstituted heteroaryl, substituted or unsubstituted heterocyclic ring, substituted or unsubstituted heterocyclylalkyl, or substituted or unsubstituted heteroarylalkyl, and Y is CH$_2$ or CHF, and (b) a compound selected from

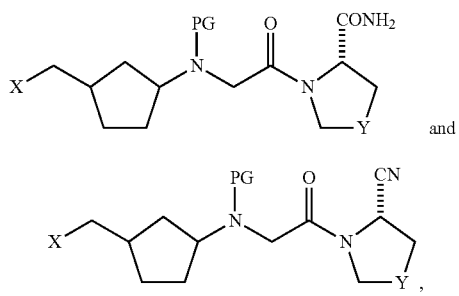

wherein PG is a suitable nitrogen protecting group selected from tert-butyloxycarbonyl, benzyloxy carbonyl, or benzyl, and X and Y are as defined, wherein the compound in component (b) is present in an amount up to 0.2% based upon 100% total weight of components (a) and (b).

8. The pharmaceutical composition of claim 7, wherein the compound in component (b) is present in an amount up to 0.1% based upon 100% total weight of component (a) and (b).

9. The pharmaceutical composition of claim 7, wherein the compound in component (a), i.e., the active component, is present in an amount greater than 95% based upon 100% total weight of components (a) and (b).

10. The pharmaceutical composition of claim 7, wherein the compound in component (a), i.e., the active component, is present in an amount greater than 98% or 99% based upon 100% total weight of components (a) and (b).

11. The pharmaceutical composition of claim 7, wherein the compound in component (a) is (2S,4S)-1-{2-[3SR,1RS)-3-(1H-1,2,4-Triazol-1-ylmethyl)cyclopentylamino]acetyl}-4-fluoro-pyrrolidine-2-carbonitrile or a pharmaceutically acceptable salt thereof.

* * * * *